US008309320B2

(12) United States Patent
Morris et al.

(10) Patent No.: US 8,309,320 B2
(45) Date of Patent: Nov. 13, 2012

(54) DIAGNOSIS OF CONDITIONS ASSOCIATED WITH DECREASED ARGININE BIOAVAILABILITY

(75) Inventors: Claudia R. Morris, Oakland, CA (US); Stanley L. Hazen, Cleveland, OH (US)

(73) Assignees: Children's Hospital & Research Center at Oakland, Oakland, CA (US); The Cleveland Clinic Foundation, Cleveland, OH (US)

( * ) Notice: Subject to any disclaimer, the term of this patent is extended or adjusted under 35 U.S.C. 154(b) by 211 days.

(21) Appl. No.: 12/628,841

(22) Filed: Dec. 1, 2009

(65) Prior Publication Data

US 2010/0196939 A1 Aug. 5, 2010

Related U.S. Application Data

(62) Division of application No. 11/293,351, filed on Dec. 1, 2005, now Pat. No. 7,648,840.

(60) Provisional application No. 60/632,572, filed on Dec. 1, 2004.

(51) Int. Cl.
*C12Q 1/34* (2006.01)
*G01N 33/50* (2006.01)
*G01N 33/00* (2006.01)
*C12P 13/10* (2006.01)
*C12N 9/14* (2006.01)
*C12N 9/78* (2006.01)
*G01N 31/00* (2006.01)
*A61K 38/00* (2006.01)

(52) U.S. Cl. .......... 435/18; 435/114; 435/195; 435/227; 436/16; 436/68; 436/86; 436/116; 514/15.7

(58) Field of Classification Search .................. None
See application file for complete search history.

(56) References Cited

U.S. PATENT DOCUMENTS

| 4,096,037 | A | 6/1978 | Mia |
| 6,720,188 | B2 | 4/2004 | Kaddurah-Daouk et al. |
| 7,648,840 | B2 * | 1/2010 | Morris et al. .................. 436/89 |
| 7,651,846 | B2 * | 1/2010 | Morris ............................ 435/18 |
| 2003/0003162 | A1 | 1/2003 | Rath |

FOREIGN PATENT DOCUMENTS

| EP | 0 441 119 A2 | 1/1991 |
| JP | 63059899 A | 3/1988 |
| WO | WO 99/19295 | 4/1999 |
| WO | WO 99/43308 | 9/1999 |
| WO | WO 01/78717 A1 | 10/2001 |
| WO | WO 02-23163 | 3/2002 |
| WO | WO 2004/073623 | 9/2004 |

OTHER PUBLICATIONS

Lau, T et al "Arginine, Citrulline, and Nitric Oxide Metabolism in End-Stage Renal Disease Patients" J. Clin. Invest., May 2000, 105(9), 1217-1225.*
Pearson, D.L. et al "Neonatal Pulmonary Hypertension: Urea-Cycle Intermediates, Nitric Oxide Production, and Carbamoyl-Phosphate Synthetase Function" New Engl. J. Med.,2001, 344(24), pp. 1832-1838.*
Morris et al. Journal of Pediatric Hematology/Oncology. 2000. 22:515-520.
Morris et al. Blood 2002. 100:452a (abstr 1755, suppl 1).
Morris et al. Blood 2003102:763a (abstr2818).
Morris et al. Am J Respir Crit Care Med. Jul. 15, 2004;170(2):148-53. Epub Apr. 7, 2004.
Inselman et al. Pediatr Pulmonol. May-Jun. 1986;2(3):163-9.
Jorens et al. Eur Respir J. Feb. 1993;6(2):258-66.
Vercelli J Clin Invest. Jun. 2003;111(12):1815-7.
Zimmermann et al. J Clin Invest. Jun. 2003;111(12):1863-74 relate to microarray analysis of the expression profiles of lung tissue in two murine models of asthma revealed high levels of arginase I and arginase II activity, in association with IL-4 and IL-13 overexpression.
Schnog et al. Ann Hematol. Jun. 2004;83(6):371-5. Epub Mar. 31, 2004.
Haas et al, Pediatr Int 2002;44:670-4.
Zhang et al. Hypertension. Oct. 18, 2004.
Xu et al. FASEB J. Nov. 2004;18(14):1746-8. Epub Sep. 13, 2004.
Rodriguez et al. Clin Exp Hypertens. Jan. 2004;26(1):1-12.
Morris et al. British Journal of Haematology. 2000. 111:498-500.
Lopez et al. British Journal of Haematology. 2003. 120;532-534.
Morris et al. Blood 1998. 92:160a (abstr 644, suppl 1).
Morris et al. Blood 1998. 92:695a; Morris et al. Society for Pediatric Research 1999. 45:A876.
Morris et al. Blood 1999. 94:200a (abstr 878, suppl 1).
Morris et al. Nitric Oxide as a Therapeutic Agent in Sickle Cell Disease and Other Vascular Diseases. NIH, Bethesda, Maryland, Sep. 2000; Morris et al. Blood 2000. 96:485a (abstr 2088, suppl 1).
Morris et al. "Arginine Therapy: A New Treatment for Pulmonary Hypertension in Sickle Cell Disease?" Society of Pediatric Research Annual Meeting, Baltimore, MA, Apr. 26-30, 2001; Featherston et al. *Am J Physiol.* 1973;224:127-9.
Morris et al. Blood 2001; 98:785a(abstr 3262, suppl 1).
Morris et al. Blood 2001; 98: 487a (abstr 2033, suppl 1).
Morris et al. Nitric Oxide 2002;6:435.
Lopez et al. Academic Emergency Medicine. 2002; 9(5):409.
Morris et al. Blood 2002. 100:452a (abstr 1754, suppl 1).
Lopez et al. Blood 2002; 100:452a (abstr 1752, suppl 1).
Styles et al. Blood 2002; 100:452a (abstr 1750, suppl 1).
Morris et al. J Invest Med 2003;51:S386 (abstr 169, suppl 2).
Morris et al. "Arginine Therapy in Sickle Cell Disease: A New Treatment for Pulmonary Hypertension?" Society for Pediatric Research, May 2003, (abstr 2088), 1 page.
Morris et al. "Arginine therapy: a new treatment for pulmonary hypertension in sickle cell disease?" Am J Respir Crit Care Med. Jul. 1, 2003;168(1):63-9. Epub Mar. 5, 2003.

(Continued)

*Primary Examiner* — Chris R Tate
*Assistant Examiner* — Aaron J Kosar
(74) *Attorney, Agent, or Firm* — Paula A. Borden; Bozicevic, Field & Francis LLP.

(57) ABSTRACT

The invention features methods and compositions for diagnosis, including prognosis, of conditions associated with decreased arginine bioavailability (which can result from dysregulated arginine metabolism, e.g., due to increased arginase activity) by assessing in a sample from a subject the ratio of arginine to one or more, usually two or more, modulators of arginine bioavailability. In one embodiment, the ratio of arginine to (ornithine+citrulline) is assessed to aid in diagnosis.

17 Claims, 6 Drawing Sheets

OTHER PUBLICATIONS

Morris et al. "Hydroxyurea and Arginine Therapy: Impact on Nitric Oxide Production in Sickle Cell Disease" J. Pediatric Hematology/Oncology, Aug. 2003;25:629-34.

Closs et al. Membrane transport of L-arginine and cationic amino acid analogs. In: Ignarro LJ, ed. Nitric Oxide. Biology and Pathobiology. San Diego: Academic Press; 2000:225-241.

Vallance et al. Clin Sci. 2001;100:159-60.

Cooke et al. Nitric oxide and vascular disease. In: Ignarro LJ, ed. *Nitric Oxide: Biology and Pathology.* New York: Academic Press; 2000:759-783.

Stuhlinger et al. *Circulation.* 2003;108:933-38.

Boger et al. *Semin Thromb Hemost.* 2000;26:539-45.

Ogawa et al. *J Biol Cem.* 1989;264:10205-9.

Stuhlinger et al. *Circulation.* 2001;104:2569-75.

Graham et al. *JAMA.* 1997;277:1775-81.

de Jonge et al. *J Nutr.* 2001;131:2732-40.

Lowenthal et al. *J Am Coll Nutr.* 2000;19:608-12.

Morris *Biochem J.* 1998;336:1-17.

Featherston et al. *Am J Physiol.* 1973;224:127-9.

Morris et al. Society for Pediatric Research 1999. 45:A876.

Morris et al. Blood 2000. 96:485a (abstr 2088, suppl 1).

Tang et al. Diminished Global Arginine Bioavailability and Increased Arginine Catabolism as Metabolic Profile of Increased Cardiovascular Risk. Journal of the American College of Cardiology, 2009, vol. 53, No. 22, pp. 2061-2069.

Noppen et al., "Magnesium treatment for Asthma: Where do we stand" Chest, 2002, vol. 122, No. 2, pp. 396-398.

Vichinsky et al., "New Therapies in Sickle Cell Disease", The Lancet, Lancet Limited 2002, vol. 360, No. 9333, pp. 629-631.

Yoshihide et al., "Prolonged Administration of L-arginine ameliorates chronic pulmonary hypertension and pulmonary vascular remodeling in rats." Biosis, 1998, XP002422425, 1 page.

Manteuffel-Cymborowska, Malgorzata; Chmurzyska, Wanda; Peska, Magdalena; and Grzelakowska-Sztabert, Barbara. Tumour effect on arginine/ornithine metabolic relationship in hypertrophic mouse kidney. Molecular and Cellular Biochemistry. 1997, 168(1-2), 51-57.

Hanzawa, K. et al. Relation between ARGase Type and BA System of Free Amino Acid Type and Concentrations of Arginine and Ornithine in Horse Erythrocytes. Jpn. J. Zootech. Sci. 1986, 57(9), 758-764.

Albina, J.E., et al. Role of Ornithine as a Precursor in Healing Wounds. J. Surgical Research, 1993, 55, 97-102.

Nuttall, K. L. et al. Delayed separation and the Plasma Amino Acids Arginine and Ornithine. Annals of Clinical and Laboratory Science. Nov.-Dec. 1998, 28(6), pp. 354-359.

\* cited by examiner

A.

B.

A.

B.

DIAGNOSIS OF CONDITIONS ASSOCIATED WITH DECREASED ARGININE BIOAVAILABILITY

CROSS-REFERENCE

This application is a divisional of U.S. patent application Ser. No. 11/293,351, filed Dec. 1, 2005, now U.S. Pat. No. 7,648,840, and claims the benefit of U.S. Provisional Patent Application No. 60/632,572, filed Dec. 1, 2004. U.S. patent application Ser. No. 11/293,351 and U.S. patent application Ser. No. 60/632,572 are incorporated herein by reference in their entirety.

GOVERNMENT RIGHTS

This invention was made with government support under federal grant nos. RR0127119 and HL-04386-01 awarded by the National Institutes of Health. The United States Government has certain rights in this invention.

FIELD OF THE INVENTION

The present invention is in the field of therapy and diagnosis of conditions associated with elevated arginase as described herein, including cardiovascular disease, asthma, sickle cell disease, and pulmonary hypertension.

BACKGROUND OF THE INVENTION

L-Arginine (Arg) is a conditionally essential amino acid, naturally found in dietary protein.

It is converted to nitric oxide (NO) (Palmer et al. Nat Med 1987; 327:524-526; Moncada et al. N Engl J Med 1993; 329:2002-2012; Kam et al. Anaesthesia 1994; 49:515-521) and bronchodilator (Zoritch et al. Arch Dis Child 1995; 72:259-262; Gaston et al. Am J Respir Crit Care Med 1994; 149:538-551), a potent vasodilator, by a family of enzymes known as nitric oxide synthase (NOS). NO is an essential molecule that plays a role in a broad range of functions from vascular regulation, neurotransmission (Moncada et al. 1993, supra), host defense, and cytotoxicity (Nathan et al. Proc Natl Acad Sci 2000; 97:8841-8848) to physiologic control of airways (Gaston et al. 1994, supra). Under conditions of low L-arginine concentration, nitric oxide synthase is uncoupled and reduces oxygen ($O_2$) to superoxide ($O_2^-$) instead of generating nitric oxide (Xia et al. Proc Natl Acad Sci 1996; 93:6770-6774; Dias-Da-Motta et at Brit J Haematol 1996; 93:333-340). Nitric oxide reacts rapidly with superoxide to form reactive nitric oxide species (RNOS) that could lead to worsening inflammation, oxidative stress and cellular damage (Demiryurek et al. Pharm Toxicology 1998; 82:113-117).

Recently, expression of inducible NO synthase, the enzyme that catalyzes the production of NO from L-Arg, has been found in the epithelium of asthmatic patients but not in healthy non-asthmatic patients (Hamid et al. Lancet 1993; 342:1510-1513: Nijkamp et al. Arch Int Pharmoocodyn 1995; 329:81-96). Asthmatics have exhaled air NO levels that are 3.5 times higher than non-asthmatics, which are correlated with decrease in $FEV_1$ and are affected by therapy Kharitonov et al. Eur Respir J 1995; 8:295-7). Blocking of NO production by L-Arg analogues results in an increase in allergen-induced bronchoconstriction (Ricciardolo et al. Lancet 1996; 348:374-377). A deficiency of NO is involved in airway hyperreactivity (Meurs et al. Br J Pharmacol 1999; 126:559-562). Although asthma is clearly a multifactorial disease, there is some evidence that NO may play an important role in disease pathogenesis (Sanders et al. Am J Respir Cell Mol Biol 1999; 21:147-149). For reviews, see, e.g., Dweik Cleve Clin J Med. 2001 June; 68(6):486, 488, 490, 493; Gianetti et al. Eur J Clin Invest. 2002 August; 32(8):628-35.

Arginase is an enzyme that hydrolyzes Arg to produce ornithine (Orn) and urea, (Boucher et al. Cell Mol Life Sci 1999; 55:1015-1028) however, in the presence of nitric oxide synthase (NOS), arginine is converted to nitric oxide (NO) and citrulline (Cit) (Moncada et al. 1993, supra). The expression of arginase can be induced by a variety of cytokines involved in the inflammatory process (Solomons et al. Pediatr 1972; 49:933), particularly the Th2 cytokines. (Mori et al. 2000. Relationship between arginase activity and nitric oxide production. In L. Ignarro, editor. Nitric Oxide. Biology and Pathology. Academic Press, San Diego. 199-208).

Increased serum arginase activities have been reported in patients with sickle cell disease (SCD) at steady-state (Waugh et al. Nutritional Research 1999; 19:501-518), as well as in an asthma animal model (Meurs et al. Br J Pharmacol 2002; 136:391-398). Arginase activity is elevated in SCD patients with pulmonary disease (Morris et al. Am J Respir Crit. Care Med 2003; 168:63-69; Morris et al. 2002. Elevated serum arginase activity in patients with sickle cell disease and pulmonary hypertension. The 30th Anniversary of the National Sickle Cell Program, Washington, D.C.). Plasma arginase activity appears to be related to hemolysis, associated with several markers of hemolytic severity, including plasma cell-free hemoglobin ($\rho=0.56$, $p<0.001$) LDH ($\rho=0.35$, $p<0.001$), AST ($\rho=0.34$, $p<0.001$), and Hct ($\rho r=-0.20$, $p<0.001$) (Morris et al, Erythrocyte arginase release during hemolysis contributes to endothelial dysfunction and pulmonary hypertension, $27^{th}$ Annual Meeting of the National Sickle Cell Disease Program, Los Angeles, Calif.; April 2004).

Arginase controls the metabolism of arginine into ornithine, which in turn gives rise to proline and polyamines (Mori et al. 2000, supra; Morris Annu Rev Nutr 2002; 22:87-105; Morris 2000. Regulation of arginine availability and its impact on NO synthesis. Nitric Oxide. Biology and Pathobiology. Academic Press, San Diego. 187-197; Mon et al. Biochem Biophys Res Commun 2000; 275:715-719). These downstream products of arginase activity may play a significant role in the pathogenesis of asthma, pulmonary hypertension and other inflammatory conditions, since proline is involved in collagen formation (Kershenobich et al. J Clin Invest 1970; 49:2246-2249; Albina et al. J Surg Res 1993; 55:97-102) and lung fibrosis (Endo et al. Am J Physiol Lung Cell Mol Physiol 2003; 285:L313-L321), processes that occur in airway wall thickening and airway remodeling and vascular remodeling (Tanaka et al. Inflamm Res 2001; 50:616-624: Elias et al. J Clin Invest 1999; 104:1001-1006; Elias et al. J Clin Invest 2003; 111:291-297; Busse et al. N Engl J Med 2001; 344:350-362).

Both asthmatic patients (Lopez da Mata et al. 1998. How does nitrates in blood correlated to exhaled levels in asthma? European Respiratory Conference, Geneva, Switzerland.) and SCD patients also have elevated $NO_x$ levels at baseline (Rees et al. Br J Haematol 1995; 91:834-7). Serum L-Arg and $NO_x$ levels fall during the vaso-occlusive complications of SCD, (Morris et al. J Pediatr Hematol Oncol 2000; 22:515-520) with lowest levels found during acute chest syndrome (pneumonia). Most SCD patients with pulmonary disease have a component of reactive airways that respond to bronchodilators, even though they often do not demonstrate the classical wheezing on physical exam that is usually associated with asthma. Asthma in SCD is often unrecognized and undertreated, and occurs in 30-60% of patients (Minter et al. Am J Respir Crit. Care Med 2001; 164:2016-2019).

Diagnosis and therapies based upon a more insightful understanding of the underlying mechanisms of these diseases are needed so as to provide a more rational approach to therapy. The present invention addresses these needs.

Literature

WO 2004/073623; Morris et al. Ambulatory Pediatrics Association Program and Abstracts May 1999:A197; Morris et al. Journal of Pediatric Hematology/Oncology. 2000. 22:515-520; Morris et al. "Elevated Serum Arginase Activity in Patients with Sickle Cell Disease and Pulmonary Hypertension". The 30th Anniversary of the National Sickle Cell Program, Washington D.C., September 2002; Morris et al. Blood 2002. 100:452a (abstr 1755, suppl 1).

Morris et al. "Elevated arginase activity and limited arginine bioavailability may play a role in the pathogenesis of asthma." Society of Pediatric Research, May 2003; Morris et al. Blood 2003; 102:763a (abstr2818); Zhang et al. Annual Proteomic Society Meeting, San Francisco, October 2003.

Morris et al. "Elevated arginase activity and limited arginine bioavailability: A common feature of asthma and sickle cell disease." The 27th Annual Meeting of the National Sickle Cell Program, Los Angeles, April 2004; Morris et al. "Erythrocyte arginase release during hemolysis contributes to endothelial dysfunction and pulmonary hypertension." The 27th Annual Meeting of the National Sickle Cell Program, Los Angeles, April 2004; Morris et al. "Elevated arginase activity limits arginine and nitric oxide bioavailability: A common feature of asthma and sickle cell disease." The 3rd International Conference on the Biology, Chemistry and Therapeutic Applications of Nitric Oxide. Nara, Japan, May 2004; Morris et al. "Decreased L-Arginine bioavailability and elevated arginase activity in sickle cell disease: A novel pathway towards pulmonary hypertension?" The 3rd International Conference on the Biology, Chemistry and Therapeutic Applications of Nitric Oxide. Nara, Japan, May 2004; Morris et al. "Elevated arginase activity limits arginine and nitric oxide bioavailability: A common feature of asthma and sickle cell disease." Bronchitis VII: On the crossroads of asthma and COPD. Gronigen, The Netherlands, August 2004; Morris et al. Am J Respir Crit. Care Med. 2004 Jul. 15; 170(2):148-53. Epub 2004 Apr. 7.

Inselman et al. Pediatr Pulmonol. 1986 May-June; 2(3): 163-9; Jorens et al. Eur Respir J. 1993 February; 6(2):258-66; Vercelli J Clin Invest. 2003 June; 111(12):1815-7 and Zimmermann et al. J Clin Invest. 2003 June; 111(12):1863-74 relate to microarray analysis of the expression profiles of lung tissue in two murine models of asthma revealed high levels of arginase I and arginase II activity, in association with IL-4 and IL-13 overexpression; Schnog et al. Ann Hematol. 2004 June; 83(6):371-5. Epub 2004 Mar. 31. Haas et al, Pediatr Int 2002; 44:670-4.

Zhang et al. Hypertension. 2004 Oct. 18 [Epub ahead of print]; Xu et al. FASEB J. 2004 November; 18(14):1746-8. Epub 2004 Sep. 13; Rodriguez et al. Clin Exp Hypertens, 2004 January; 26(1):1-12.

Morris et al. British Journal of Haematology. 2000. 111: 498-500; Lopez et al. British Journal of Haematology. 2003. 120; 532-534; Morris et al. Blood 1998. 92:160a (abstr 644, suppl 1); Morris et al. Blood 1998. 92:695a; Morris et al. Society for Pediatric Research 1999. 45:A876; Morris et al. Blood 1999. 94:200a (abstr 878, suppl 1).

Morris et al. The 24$^{th}$ Annual Meeting of the National Sickle Cell Disease Program, Philadelphia, Pa. 2000; Morris et al. Nitric Oxide as a Therapeutic Agent in Sickle Cell Disease and Other Vascular Diseases. NIH, Bethesda, Md., September 2000; Morris et al. Blood 2000. 96:485a (abstr 2088, suppl 1); Morris et al. "Arginine Therapy: A New Treatment for Pulmonary Hypertension in Sickle Cell Disease?" Society of Pediatric Research Annual Meeting, Baltimore, Mass., Apr. 26-30, 2001; Morris et al. Blood 2001; 98:785a (abstr 3262, suppl 1); Morris et al. Blood 2001; 98: 487a (abstr 2033, suppl 1); Morris et al. Nitric Oxide 2002; 6:435; Morris et al. Nitric Oxide 2002; 6:435; Lopez et al. Academic Emergency Medicine. 2002; 9(5):409; Morris et al. "Arginine Therapy in Sickle Cell Disease: A New Treatment for Pulmonary Hypertension?" The 30$^{th}$ Anniversary of the National Sickle Cell Program, Washington D.C., September 2002; Lopez et al. "Is 1-arginine, the substrate for nitric oxide, altered in adult vasoocclusive sickle cell crisis?" The 30$^{th}$ Anniversary of the National Sickle Cell Program, Washington D.C., September 2002; Styles et al. "Low Dose Oral Arginine Upregulates Nitric Oxide Production in Patients with Acute Chest Syndrome." The 30$^{th}$ Anniversary of the National Sickle Cell Program, Washington D.C., September 2002; Morris et al. Blood 2002. 100:452a (abstr 1754, suppl 1); Lopez et al. Blood 2002; 100:452a (abstr 1752, suppl 1); Styles et al. Blood 2002; 100:452a (abstr 1750, suppl 1); Morris et al. J Invest Med 2003; 51:S386 (abstr 169, suppl 2); Morris et al. "Arginine Therapy in Sickle Cell Disease: A New Treatment for Pulmonary Hypertension?" Society for Pediatric Research, May 2003.

Morris et al. "Arginine therapy: a new treatment for pulmonary hypertension in sickle cell disease?" Am J Respir Crit. Care Med. 2003 Jul. 1; 168(1):63-9. Epub 2003 Mar. 5; Morris et al. "Hydroxyurea and Arginine Therapy: Impact on Nitric Oxide Production in Sickle Cell Disease" J. Pediatric Hematology/Oncology, 2003 August; 25:629-34.

Closs et al. Membrane transport of L-arginine and cationic amino acid analogs. In: Ignarro L J, ed. *Nitric Oxide. Biology and Pathobiology*. San Diego: Academic Press; 2000:225-241; Valiance et al. *Clin Sci.* 2001; 100:159-60; Cooke et al. Nitric oxide and vascular disease. In: Ignarro L T, ed. *Nitric Oxide: Biology and Pathology*. New York: Academic Press; 2000:759-783; Stuhlinger et al. *Circulation.* 2003; 108:933-38; Boger et al. *Semin Thromb Hemost.* 2000; 26:539-45; Ogawa et al. *J Biol Cem.* 1989; 264:10205-9; Stuhlinger et al. *Circulation.* 2001; 104:2569-75; Graham et al. *JAMA.* 1997; 277:1775-81; Stuhlinger et al. *Circulation.* 2001; 104:2569-75; de Jonge et al. *J Nutr.* 2001; 131:2732-40; Graham et al. *JAMA.* 1997; 277:1775-81; Lowenthal et al. *J Am Coll Nutr.* 2000; 19:608-12; Morris *Biochem J.* 1998; 336:1-17; Featherston et al. *Am J Physiol.* 1973; 224:127-9.

SUMMARY OF THE INVENTION

The invention features methods and compositions for diagnosis, including prognosis, of conditions associated with decreased arginine bioavailability (which can result from dysregulated arginine metabolism, e.g., due to increased arginase activity) by assessing in a sample from a subject the ratio of arginine to one or more, usually two or more, modulators of arginine bioavailability. In one embodiment, the ratio of arginine to (ornithine+citrulline) is assessed to aid in diagnosis.

As used herein, modulators of arginine bioavailability are compounds that affect metabolism of arginine. Such modulators include substrates or products of an arginine metabolism pathway (e.g., nitric oxide synthase (NOS), arginase, and the like), as well as compounds that promote or inhibit activity of an amino acid transporter or enzyme involved in an arginine metabolism pathway (e.g., NOS, arginase, and the like; see FIG. 6 for review of arginine pathway involving NOS and arginase). Exemplary modulators include amino acids and metabolites of amino acids that are metabolites of arginine or are metabolized to arginine, metabolites from enzymes that directly produce or utilize arginine, including but not limited to NOS and arginase, or metabolites that result from metabolism of citrulline to arginine in the kidney (which is reduced under condition of renal insufficiency or dysfunction/injury), and amino acid metabolites that impact transport of arginine or represent arginine analogues (methylated arginines) thereby impacting arginine bioavailability. The calculation of the final ratio of arginine to such modulators are reflective of global arginine bioavailability, or local arginine bioavailability particularly with respect to a certain organ system, location or cell type.

The invention is advantageous in that patients can be more accurately diagnosed as to the nature of the disease, whether the disease is amenable to treatment using arginine-based or arginase inhibitor-based therapy, the severity of the disease, and the responsiveness of the patient to therapy.

The invention also provides the advantage that a simple, relatively inexpensive assay provides a sensitive method of diagnosis of disease, as well as a measure of disease severity.

These and other advantages will be apparent to the ordinarily skilled artisan upon reviewing the present specification.

DEFINITIONS

Figure 1:
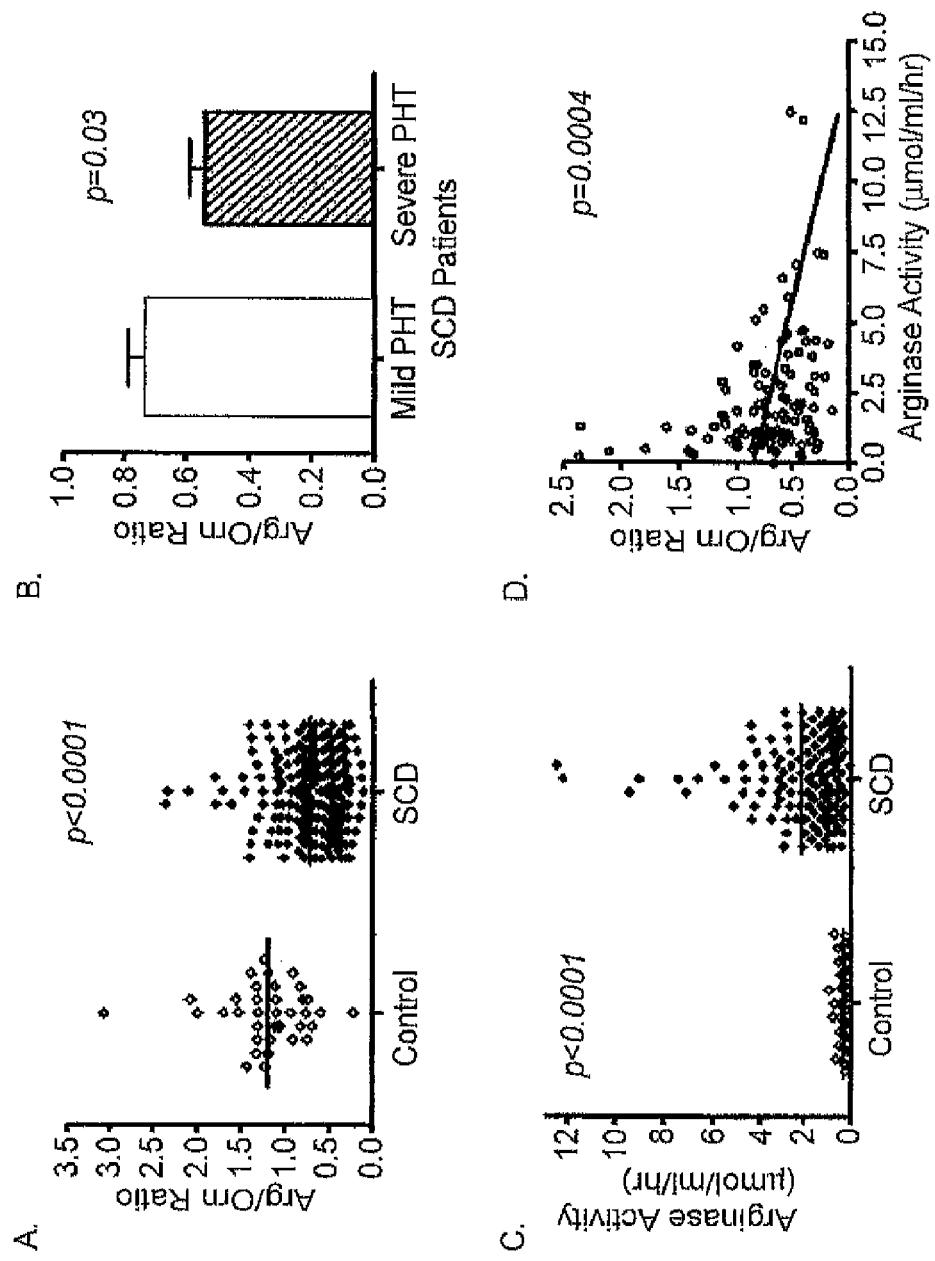
FIG. 1 is a set of graphs showing that the arginine-to-ornithine ratio as a surrogate marker for arginase activity, its association with pulmonary hypertension and correlation with arginase activity. Panel A. The arginine-to-ornithine ratio (Arg/Orn) in normal controls (Control, n=36) vs. patients with SCD (n=209). Panel B. Arginine-to-ornithine ratio in sickle cell patients with a tricuspid regurgitant jet velocity (TRV) by echocardiography 2.5-2.9 m/s (mild PHT) vs. patients with a TRV≧3.0 m/s (severe PHT). Panel C. Plasma arginase activity (μmol/ml/hr) in normal controls (Control, n=45) vs. patients with sickle cell disease (SCD, n=140). Panel D. Correlation of plasma arginase activity to the arginine-to-ornithine ratio.

"Arginine" or "Arg" or "L-Arg" as used herein refers to naturally occurring or synthetically produced L-arginine.

"Arginase" as used herein refers to an enzyme that mediates conversion of L-Arg into ornithine and urea, and is meant to encompass any or all relevant arginase types, including, for example, arginase type I, arginase type II, and the like.

"Arginine metabolite" as used herein is generally meant to refer to a product of action of nitric oxide synthase (NOS) or arginase on arginine, as well as metabolites from arginine: glycine amidinotransferase and arginine decarboxylase activity on arginine. "Arginine metabolite" can include immediate metabolites of NOS, arginase or other arginine catabolizing enzymes' action upon arginine (e.g., citrulline, ornithine, creatine and the like) or downstream products of such metabolites (e.g. proline, polyamines and the like).

"Arginine bioavailability" or "bioavailable arginine" refers to arginine that is available for normal physiologic metabolism/catabolism. Bioavailability of arginine can be adversely impacted (decreased) by many factors, including but not limited to low plasma concentration, abnormal arginine transporter function, competitive inhibition, the presence of arginine analogues (including but not limited to methylated arginine and other NOS inhibitors), poor nutrition, function of de novo synthesis of arginine (i.e. aberrations in the intestinal-renal axis such as renal dysfunction, poor nutrition, intestinal malabsorption of glutamate, small bowel dysfunction, or catabolic states such as sepsis, trauma, burn injury, post-operative surgery, and the like).

A "condition of decreased arginine bioavailability" refers generally to a condition or disease in which arginine bioavailability is decreased relative to an unaffected individual. In the context of the present invention, patients having such conditions have an Arg/modulator(s) ratio value that is less than 75% of a normal Arg/modulator(s) ratio value.

A "modulator of arginine bioavailability" as used herein refers to a compound that facilitates a decrease in arginine bioavailability. Such modulators include substrates or products of an arginine metabolism or catabolism pathway (e.g., nitric oxide synthase (NOS), arginase, and the like), as well as compounds that promote or inhibit activity of an amino acid transporter or enzyme involved in an arginine metabolism pathway (e.g., NOS, arginase, and the like).

"Pulmonary hypertension" (or "PH" or "PAH") as used herein is generally meant to refer to a blood vessel disorder of the lung in which the pressure in the pulmonary artery rises above normal levels. Symptoms of pulmonary hypertension include shortness of breath with minimal exertion, fatigue, chest pain, dizzy spells and fainting. When pulmonary hypertension occurs in the absence of a known cause, it is referred to as primary pulmonary hypertension (PPH). Secondary pulmonary hypertension indicates the cause is known. A common cause of secondary pulmonary hypertension are the breathing disorders emphysema and bronchitis. Other less frequent causes are the inflammatory or collagen vascular diseases such as scleroderma, CREST syndrome or systemic lupus erythematosus (SLE). Congenital heart diseases that cause shunting of extra blood through the lungs like ventricular and atrial septal defects, chronic pulmonary thromboembolism (old blood clots in the pulmonary artery), HIV infection, liver disease and diet drugs like fenfluramine and dexfenfluramine are also causes of pulmonary hypertension. Prior to the present invention, pulmonary hypertension is frequently misdiagnosed and has often progressed to late stage by the time it is accurately diagnosed.

As used herein, the term "diagnosis" can encompass determining the nature of disease in a subject, as well as determining the severity and probable outcome of disease or episode of disease and/or prospect of recovery (prognosis). "Diagnosis" can also encompass diagnosis in the context of rational therapy, in which the diagnosis guides therapy, including initial selection of therapy, modification of therapy (e.g., adjustment of dose and/or dosage regimen), and the like.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and can include: (a) preventing the disease or a symptom of a disease from occurring in a subject which may be predisposed to the disease but has not yet been diagnosed as having it (e.g., including diseases that may be associated with or caused by a primary disease); (b) inhibiting the disease or condition, i.e., arresting its development; and (c) relieving the disease, i.e., causing regression of the disease.

The terms "individual," "host," "subject," and "patient" are used interchangeably herein, and generally refer to a mammal, including, but not limited to, primates, including simians and humans, equines (e.g., horses), canines (e.g., dogs), felines, various domesticated livestock (e.g., ungulates, such as swine, pigs; goats, sheep, and the like), as well as domesticated pets and animals maintained in zoos. Treatment of humans is of particular interest.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a sample" includes a plurality of such samples and reference to "the arginase" includes reference to one or more arginase polypeptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention is based on the discovery that arginine bioavailability, which is impacted by, for example, arginase activity, can be assessed by calculating the ratio of arginine to one or more, usually two or more compounds that effect a decrease in arginine bioavailability, such as amino acids and/or amino acid metabolites produced as a result of arginine metabolism, catabolism, and/or transport (e.g., products of NOS activity, arginase activity, arginine:glycine amidinotransferase and arginine decarboxylase), as well as downstream by-products of such enzymes (e.g., citrulline, ornithine, creatine and the like).

This discovery led to the insight that low arginine bioavailability plays a role in a variety of different conditions, and thus the presence of compounds that contribute or further contribute to decreased arginine bioavailability can exacerbate such conditions. Such compounds that serve to effect a decrease in arginine bioavailability are referred to herein as "modulators of arginine bioavailability" (or "modulators" for convenience). Such modulators include substrates or products of an arginine metabolism pathway (e.g., nitric oxide synthase (NOS), arginase, and the like), as well as compounds that promote or inhibit activity of an amino acid transporter or enzyme involved in an arginine metabolism pathway (e.g., NOS, arginase, and the like).

Exemplary modulators include amino acids and metabolites of amino acids that are metabolites of arginine or are metabolized to arginine, metabolites from enzymes that directly produce or utilize arginine, including but not limited to NOS and arginase, or metabolites that result from metabolism of citrulline to arginine in the kidney (which is reduced under condition of renal insufficiency or dysfunction/injury), and amino acid metabolites that impact transport of arginine or represent arginine analogues (methylated arginines) thereby impacting arginine bioavailability.

Specific exemplary modulators include competitive inhibitors of arginine transport and/or NOS isozymes (e.g., methylarginines (including symmetric and asymmetric dimethylarginine [ADMA] and $N^G$-monomethyl-L-arginine [NMMA]), metabolites of methylarginines, inhibitors of enzymes that metabolize methylarginines (e.g., inhibitors of the enzyme dimethylarginine dimethylaminohydrolase (DDAH), such as homocysteine), creatine, downstream by-products of arginase activity (e.g., proline and polyamines), and the like. The calculation of the final ratio of arginine to such a modulator(s) is reflective of global arginine bioavailability, or local arginine bioavailability particularly with respect to a certain organ system, location or cell type.

Although the underlying mechanisms that lead to a decrease in Arg bioavailability can differ, the present invention can be used to assess diagnosis of the condition. The only requirement is that Arg bioavailability be adversely impacted.

For example, arginase plays a role in modifying L-Arg bioavailability in SCD, asthma, pulmonary hypertension, and other pathologic conditions of upregulated arginase activity. Increased arginase activity limits arginine bioavailability through its conversion of L-Arg to ornithine and urea, thereby competing with NOS for available L-Arg substrate and regulating nitric oxide (NO) production. Ornithine itself also decreases L-Arg bioavailability, since both L-Arg and ornithine compete for the same transport system for cellular uptake. Downstream by-products of arginase activity, e.g., proline and polyamines, have been implicated in lung and cardiovascular pathology, by way of airway remodeling, fibrosis and vascular smooth muscle proliferation. In addition to decreasing NO bioavailability, elevated arginase activity also provides substrate for a pathway which produces metabolites that likely play a role in the pathogenesis of cardiovascular disease, lung fibrosis, asthma, pulmonary hypertension and other inflammatory conditions.

Figure 6:
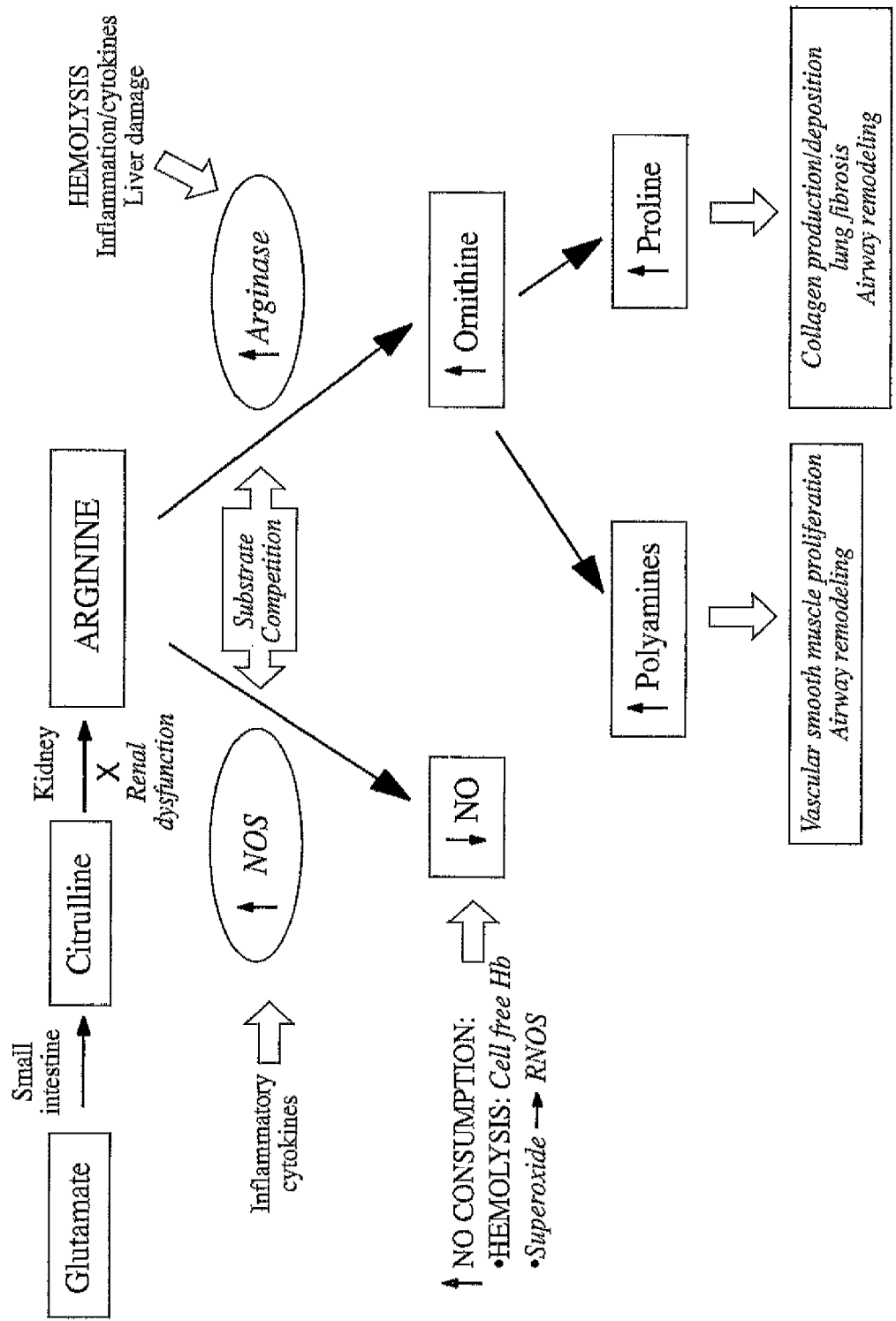
FIG. 6 is a schematic illustrating altered arginine metabolism. Arginine is synthesized endogenously primarily via the intestinal-renal axis. Stimuli that increase activities of nitric oxide synthase (NOS) and arginase are indicated, as are conditions that result in increased NO consumption. Potential consequences of elevated ornithine production are also indicated.

Without being held to theory, the present invention is further based on the hypothesis that arginase plays a role in modifying L-Arg bioavailability in pathologic conditions that involve upregulation of arginase levels/activity. Increased arginase activity limits arginine bioavailability through its conversion of L-Arg to ornithine and urea, thereby competing with nitric oxide synthase (NOS) for available L-Arg substrate and interfering with NO production (FIG. 6). L-Arg produces nitric oxide (NO) and citrulline (cit) in the presence of the nitric oxide synthase enzyme (NOS). Nitric oxide release causes vasodilation through the activation of soluble guanylate cyclase (GTP) to the intracellular messenger cyclic GMP (cGMP). Arginase converts L-arginine to ornithine and urea. Both L-arginine and ornithine use the same Cationic Amino Acid Transporter molecule (CAT) for cellular uptake. Ornithine can competitively inhibit L-arginine transport into the endothelial cell, thereby limiting substrate availability for nitric oxide synthase and regulating nitric oxide production. NG-hydroxyl-L-arginine is the intermediate product of the L-arginine-nitric oxide pathway, and is a potent inhibitor of arginase activity.

Accumulation of both intracellular and extracellular NG-hydroxyl-L-arginine favors the continued conversion of L-arginine to nitric oxide by maintaining adequate arginine availability. The downstream by-products of arginase activity, i.e., proline and polyamines, thus can play a role in disease pathogenesis, as they are involved in vascular smooth muscle proliferation as well as airway remodeling (FIG. 6). These metabolites may accumulate in serum or plasma as seen in sickle cell patients with pulmonary hypertension. This is a novel model for the pathogenesis of pulmonary hypertension.

Similarly, praline is involved in collagen formation and lung fibrosis, processes that occur in airway wall thickening and airway remodeling. Proline plays an important function in tissue remodeling and normal wound healing, however overproduction can lead to pathologic states. Elevated arginase activity can lead to such conditions.

Since both arginase and NOS use Arg as a common substrate, arginase plays a role in regulating nitric oxide (NO) synthesis by modulating L-Arg availability. For example, in an environment of low L-arginine concentration, nitric oxide synthase is uncoupled and reduces oxygen ($O_2$) to superoxide ($O_2^-$) instead of generating nitric oxide. Nitric oxide reacts rapidly with superoxide to form reactive nitric oxide species (RNOS) that could lead to oxidative stress and cellular damage. Pathological conditions of increased arginase activity thus have a negative impact on nitric oxide bioavailability. Decreased arginine bioavailability leads to hyperreactive airways in both SCD and asthma, since it plays a role in bronchodilation. Thus, decreased arginine bioavailability and elevated arginase activity contributes to the disease process. Furthermore, decreased arginine bioavailability leads to pulmonary hypertension in the susceptible patient.

In another setting, hyperhomocysteinemia is a risk factor for vascular disease and thrombosis, and leads to elevated plasma ADMA levels and decreased NO production in the cardiovascular system through competitive Arg inhibition.

Another major catabolic Arg pathway results in the synthesis of creatine, a process that regulates methylation reactions such as the synthesis of methionine from homocysteine. Limited Arg bioavailability can therefore also affect creatine homeostasis in addition to its impact on NO production, potentially contributing to hyperhomocysteinemia and an accumulation of circulating methylated arginines. The role of methylated arginines, homocysteine, creatine or other metabolites that impact global arginine bioavailability are thus also contemplated as modulators of arginine bioavailability.

The data presented herein indicate that assessment of the ratio of arginine to one or more modulators of arginine bioavailability correlates with arginine bioavailability, which in turn is a marker for disease, including disease severity. For example, the ratio of arginine/(ornithine citrulline) correlates with arginine bioavailability, and is a marker of severity of disease. This observation indicates that assessment of the ratio of a level of arginine to a level of such a modulator (e.g., an arginine metabolite (e.g., ornithine, citrulline, etc.)) correlates with arginine bioavailability and thus serves as a diagnostic and marker of disease severity.

The invention will now be described in more detail.

Subjects Having Elevated Arginase Activity Amenable to Diagnosis

In general, the invention involves diagnosis of a condition having decreased arginine bioavailability, which can result from dysregulated arginine metabolism (e.g., due to elevated arginase and/or NOS activity). Diagnosis is accomplished by assessing the ratio of a level arginine in a sample from the patient to a level(s) of one or more modulators of arginine bioavailability ("modulator"), usually two or more or three or more such modulators. In most embodiments, the modulator is generally an amino acid or amino acid metabolite that accumulates in a condition of decreased arginine bioavailability (e.g., ornithine, proline, methylated arginines, polyamines, citrulline, and the like). Conditions of elevated arginase activity are of particular interest for diagnosis according to the invention. In one embodiment, the ratio is that of arginine/ornithine in a sample. In another embodiment, the ratio is that of arginine to citrulline in a sample. In one embodiment of particular interest, the ratio is that of arginine/(ornithine+citrulline) in sample. In another embodiment of particular interest, the ratio is that of arginine/(ornithine+citrulline+ADMA).

Any subject having a condition associated with decreased nitric oxide bioavailability, such as that which results from decreased arginine bioavailability, elevated arginase (e.g., arginase activity and/or arginase levels), or decreased NO bioavailability, is amenable to diagnosis according to the invention. Exemplary conditions associated with decreased nitric oxide bioavailability and/or elevated arginase levels (relative to non-disease individuals) include, but are not necessarily limited to asthma, sickle cell disease (SCD), pulmonary hypertension (neonatal pulmonary hypertension and/or persistent pulmonary hypertension of the newborn, primary hypertension, secondary hypertension, hypertension associated with SCD), pneumonia, chronic obstructive pulmonary disease (COPD), systemic hypertension, pregnancy related hypertension (pre-eclampsia/eclampsia), cardiovascular conditions, arteriosclerosis, hypercholesterolemia, diabetes, trauma injury, sepsis, cystic fibrosis, erectile dysfunction, post-operative surgery, bypass surgery, and hemolytic disorders (where the source of elevated arginase activity is via release from the red blood cell, e.g., thalassemia).

Subjects having such an elevated arginase activity condition may have or be suspected of having the condition. In addition, arginase activity in a subject can also be assessed according to the methods of the invention in order to follow therapy, e.g., to provide information to guide the clinician regarding adjustment of therapy (e.g., to change the drug administered, the dose, and/or the dosage regimen). Subjects may be undergoing therapy, have previously received therapy, or may not have been previously treated ("treatment naïve").

By "elevated arginase activity levels" is meant that the subject exhibits a level of arginase activity that is about 20% greater, usually more than about 20% greater, than arginase activity of an average normal subject. Arginase activity levels can be assessed by direct detection of arginase activity in a sample, or by assessing a ratio of arginine to ornithine amino acids (or arginine to ADMA, or a combination or Arg/(Orn+ADMA)) in a sample.

Assessment of Arginase Levels by Assessing Amino Acid Ratios in a Patient Sample and Diagnosis Based on Arginine-to-Arginine Metabolite Ratio As noted above, the present invention is based on the discovery that the ratio of a level of arginine to a level of one or more, usually two or more, in some embodiments three or more, modulators of arginine bioavailability (e.g., arginine metabolites and other downstream products, such as those generated in the arginase/NOS pathway, e.g., ornithine, citrulline, and the like) is diagnostic for a condition having decreased arginine bioavailability relative to an unaffected individual. Such ratios are generally referred to herein as the ratio of arginine bioavailability or the Arg/modulator(s) ratio.

In one embodiment, the invention involves calculating an Arg/modulator(s) ratio represented by the formula:

$$Arg/(A+B)$$

where "Arg" is a level of arginine in a sample, A is a level of a first modulator of arginine bioavailability, and B is a level of a second modulator of arginine bioavailability. A is a different modulator of arginine bioavailability from B.

As discussed above, a "modulator of arginine bioavailability" (or "modulator" for convenience) is meant to refer to a substrate or product of an arginine metabolic or catabolic pathway (e.g., a substrate or product of nitric oxide synthase (NOS), arginase, and the like), as well as compounds that promote or inhibit activity of an amino acid transporter or enzyme involved in an arginine metabolism or catabolism pathway (e.g., NOS, arginase, and the like). In general, accumulation of a modulator of arginine bioavailability is associated with a decrease in bioavailable arginine.

Exemplary modulators of arginine bioavailability include amino acids and metabolites of amino acids that are metabolites of arginine or are metabolized to arginine, metabolites from enzymes that directly produce or utilize arginine, including but not limited to NOS and arginase, or metabolites that result from metabolism of citrulline to arginine in the kidney (which is reduced under condition of renal insufficiency or dysfunction/injury), and amino acid metabolites that impact transport of arginine or represent arginine analogues (methylated argininies) thereby impacting arginine bioavailability.

Specific exemplary modulators include compounds that are competitive inhibitors with arginine for arginine transport (e.g., by arginine:glycine amidinotransferase) and/or NOS (e.g., methylarginines (including symmetric and asymmetric dimethylarginine [ADMA] and $N^G$-monomethyl-L-arginine [NMMA]), metabolites of methylarginines, inhibitors of enzymes that metabolize methylarginines (e.g., inhibitors of the enzyme dimethylarginine dimethylaminohydrolase (DDAH), such as homocysteine), creatine, downstream by-products of arginase activity (e.g., proline and polyamines), and the like.

Where the modulator of arginine bioavailability is an "arginine metabolite", the modulator is generally a product of action (either directly or downstream) of nitric oxide synthase (NOS), arginase and/or arginine decarboxylase activity on arginine. "Arginine metabolite" can include immediate metabolites of NOS, arginase and/or arginine decarboxylase action upon arginine (e.g., citrulline, ornithine, and the like) or downstream products of such metabolites (e.g., proline, polyamines).

In one embodiment the modulator of arginine bioavailability is an arginine analogue (e.g. methylated arginines, ADMA and the like), or an inhibitor of arginine cellular transport (e.g. ornithine, lysine and the like). In one embodiment the modulator of arginine bioavailability is a compound other than lysine.

In one embodiment of particular interest, the first and second modulators of arginine bioavailability are arginine metabolites. In a related embodiment, the first arginine metabolite is ornithine and the second arginine metabolite is citrulline. In another embodiment, the ratio is arginine/(ornithine+citrulline). In a further embodiment, the ratio is Arg/(ADMA+Citrulline). In yet another embodiment, the ratio is Arg/(ADMA+Ornithine)

In another embodiment, the invention involves calculating a Arg/modulator(s) ratio as represented by the formula:

$$Arg/(A+B+C)$$

where "Arg" is a level of arginine in a sample, A is a level of a first modulator of arginine bioavailability, B is a level of a second modulator of arginine bioavailability, and C is a level of a third modulator of arginine bioavailability. A, B and C are different compounds. In one embodiment each of the first, second and third modulators of arginine bioavailability are arginine metabolites. In another embodiment, the first and second modulators of arginine bioavailability are arginine metabolites and the third modulator of arginine bioavailability is a competitive inhibitor of arginine transport (e.g., ADMA). In a related embodiment of particular interest, A is ornithine, B is ADMA, and C is citrulline (i.e., the ratio is Arg/(orn+ADMA+citrulline)).

In another embodiment, compounds that positively affect arginine bioavailability are taken into account. In this embodiment, the ratio is calculated according to the formula:

$$(Arg+D)/(A+B+C)$$

where "Arg" is a level of arginine in a sample, D is a level of a compound that enhances arginine bioavailability (such as creatine), A is a level of a first modulator of arginine bioavailability, B is a level of a second modulator of arginine bioavailability, and, optionally, C is a level of a third modulator of arginine bioavailability. A, B and C are different compounds. In one embodiment, the ratio is (Arg+creatine)/(orn+ADMA+citrulline).

Reference to "level" in the discussion of Arg/modulator(s) ratio is meant to refer to a quantitative or qualitative measure, usually a quantitative measure, of an amount of the compound in a biological sample. "Levels" can be described in terms of any unit of measure so long as the values used for the level of each factor in the ratio is internally consistent (e.g., each value is provided in the ratio in the same unit of measure).

The levels of arginine and arginine bioavailability modulator(s) is measured using any method, including standard methods known in the art. Immunological assays will in some embodiments be used, where suitable immunological assays include enzyme-linked immunosorbent assay (ELISA), radioimmunoassay (RIA), and the like. Immunological assays include sandwich-type assays, competitive assays, etc. Immunological assays generally involve use of an antibody specific for arginine or an arginine bioavailability modulator, where the antibody is detectably labeled, either directly or indirectly. Suitable direct labels include, but are not limited to, radioactive labels (e.g., $^{125}$I, etc.); enzyme labels, where the enzyme generates a product that is detectable by a colorimetric or fluorimetric assay, e.g., β-galactosidase, luciferase, horse radish peroxidase, alkaline phosphatase; fluorescent proteins, e.g. a green fluorescent protein; and the like. Indirect labels include secondary antibodies that are detectably labeled; a member of a specific binding pair (e.g., biotin/avidin, etc.) that is detectably labeled; and the like. High performance liquid chromatography (HPLC), including reverse phase HPLC, will in some embodiments be used to determine a level of arginine and/or an arginine bioavailability modulator. Other suitable methods include the use of mass spectrometry, spectrophotometric methods, tandem mass spectrometry methods, etc. Suitable methods for determining a level of arginine or an arginine bioavailability modulator have been reported in the literature. See, e.g., U.S. Pat. No. 6,720,188; Teerlink et al. (2002) *Anal. Biochem.* 303:131-137; Dobashi et al. (2002) *Analyst* 127:54-59; Pi et al. (2000) *J. Chromatogr. B. Biomed Sci. Appl.* 742:199-203; Chen et al. (1997) *J. Chromatogr. B. Biomed Sci. Appl.* 692:467-471; Anderstam et al. (1997) *J. Am. Soc. Nephrol.* 8:1487-1442; Pettersson et al. (1997) *J. Chromatogr. B. Biomed. Sci. Appl.* 692:257-262; Sultana et al. (2001) *J. Chromatogr. B. Biomed. Sci. Appln.* 755:321; Chace et al. (2003) *Clin. Chem.* 49:1797-1817; and Trapp et al. (2004) *J. Sep. Sci.* 27:1483-1490.

This aspect of the invention is based on the discovery that, arginine levels in normal control patients were generally greater than levels of arginine metabolites (e.g., citrulline, ornithine, and the like), such that the Arg/(A+B) ratio as defined above often approached 1:1. However, in subjects affected by a condition having elevated arginase activity (e.g., asthma, pulmonary hypertension, sickle cell disease (SCD), or thalassemia), the Arg/(A+B) ratio (e.g., the arginine/(ornithine+citrulline) ratio) was significantly decreased (<0.75).

Without being held to theory, as the concentration of modulators of arginine bioavailability increase, (such as amino acids in the arginine cycle), and thus the Arg/modulator(s) ratio (e.g., the Arg/(A+B) ratio, e.g., Arg/(ornithine+citrulline) ratio)) decreases, arginine bioavailability becomes limited even under conditions of apparently normal arginine concentration.

For example, pathologically elevated arginase activity reduces the Arg/modulator(s) ratio of Arg/(ornithine+citrulline) by utilizing arginine (and decreasing that which is available to nitric oxide synthase to make nitric oxide), while hydrolyzing arginine to ornithine, the substrate for proline and polyamine production, metabolites likely involved in disease pathogenesis. In another example in the context of conditions of renal dysfunction, the de novo Arg synthesis in the kidney is decreased, with an accumulation of citrulline. The inventors have found that rising citrulline levels significantly correlate to rising creatinine levels (r=0.54, p<0.001). Including citrulline in the ratio above thus provides a superior biomarker of global arginine bioavailability (compared to the arg/orn ratio, for example) since it takes into consideration the impact of renal dysfunction and loss of normal de novo arginine synthesis.

A low Arg/modulator(s) ratio in a biological sample from a subject relative to a value of the ratio in a normal subject is a reflection of decreased arginine bioavailability, which can be due to, for example, increased arginase activity. For example, where the Arg/modulator(s) ratio is Arg/(A+B), once this ratio nears about 0.65 or is less than 0.65, arginine availability for nitric oxide production has reached a competitive disadvantage. An Arg/(A+B) ratio of less than about 0.8, usually less than about 0.75, more usually less than about 0.70, still more usually less than about 0.65 is considered low and indicative of a condition of decreased arginine bioavailability (e.g., elevated arginase activity).

For example, an arginine/(ornithine+citrulline) ratio that nears about 0.65 or is less than 0.65 indicates arginine availability for nitric oxide production has reached a competitive disadvantage. For example, an arginine/(ornithine+citrulline) ratio of less than about 0.70 is considered low and indicative of a condition of decreased arginine bioavailability (e.g., due to elevated arginase activity). Patients with such a finding, regardless of the disease pathology, can be treated with an appropriate therapy (e.g., L-Arg monotherapy, arginase inhibitor monotherapy, arginine/arginase inhibitor combination therapy, arginine/magnesium combination therapy, or a conventional appropriate therapy).

A patient having an Arg/(A+B) ratio of less than about 0.8, or less than about 0.75, but greater than, for example about 0.7, is generally diagnosed as having a condition in which arginine availability for nitric oxide production is at a competitive disadvantage, and thus the patient is at risk of a condition of decreased arginine bioavailability (e.g., dysregulated arginine metabolism, e.g., elevated arginase activity). For example, a patient having an arginine/(ornithine+citrulline) ratio of less than about 0.80, but greater than about 0.70 is diagnosed as being at risk of a condition of decreased arginine bioavailability (e.g., due to elevated arginase activity).

In general, a patient having an Arg/(A+B) ratio less than or equal to about 0.75 but greater than about, for example, 0.70, is diagnosed as having a borderline Arg/(A+B) ratio and is at risk of developing a condition of decreased arginine bioavailability (e.g., due to elevated arginase activity). A patient having an Arg/(A+B) ratio of about or less than about 0.70, 0.65, 0.60, 0.55, 0.50 or lower is diagnosed as having or at risk for developing a condition of decreased arginine bioavailability (e.g., due to elevated arginase activity).

In one embodiment, the Arg/(A+B) ratio is an arginine/(ornithine+citrulline) ratio. An arginine/(ornithine+citrulline) ratio less than or equal to about 0.75, but greater than about, for example, 0.70, is diagnosed as having a borderline arginine/(ornithine+citrulline) ratio and is at risk of developing a condition of decreased arginine bioavailability (e.g., due to elevated arginase activity). A patient having an arginine/(ornithine+citrulline) ratio of about or less than about 0.70 or lower is diagnosed as having or at risk for developing a condition of decreased arginine bioavailability (e.g., due to elevated arginase activity).

In some embodiments, the ratio of arginine to a single modulator (e.g., one of ornithine, citrulline, etc.) is assessed as an indicator of arginase activity level. A patient having an arginine/single modulator (e.g., arginine/ornithine, arginine/citrulline, etc.) ratio of less than about 1.2 or less than about 1.1 is diagnosed as having a condition in which arginine availability for nitric oxide production is at a competitive disadvantage, and thus the patient is at risk of a condition having elevated arginase activity. For example, in general, a patient having an arginine/modulator ratio less than or equal to about 1, but greater than about, for example, 0.95, is diagnosed as having a borderline arginine/modulator ratio and is at risk of developing a condition having elevated arginase activity. A patient having an arginine/modulator ratio of about or less than about 0.95, 0.8, 0.7, 0.6 or lower is diagnosed as having or at risk for developing a condition having elevated arginase activity. In some embodiments, a patient having an arginine/modulator ratio of about or less than about 0.95, 0.8, 0.7, 0.6 or lower is diagnosed as having or at risk for developing cardiovascular disease.

A patient who presents with an arginine/modulator ratio of about 0.6, 0.5, 0.4, 0.3, 0.2, or lower has or is at risk of an elevated arginase condition of a greater severity than a patient who presents with an arginine/modulator ratio of 1.0. In general, an arginine/modulator ratio that is not equal to or greater than normal but is at least about 75%, 80%, or 85% of the value of normal arginine/modulator ratio indicates the subject has or is at risk of an elevated arginase condition. If the arginine/modulator ratio value is more than 25% reduced from the normal arginine/modulator ratio value, then the subject is diagnosed has having a condition of elevated arginase activity. The lower the arginine/modulator ratio value relative to a normal arginine/modulator ratio value, the greater the severity of the disease. In particular embodiments of interest, a patient who presents with an arginine/modulator ratio of about 0.6, 0.5, 0.4, 0.3, 0.2, or lower has or is at risk of cardiovascular disease of a greater severity than a patient who presents with an arginine/modulator ratio of 1.0. In some embodiments, a patient who presents with an arginine/modulator ratio of about 0.6, 0.5, 0.4, 0.3, 0.2, or lower has an increased mortality risk compared to a patient who presents with an arginine/modulator ratio of 1.0.

Amino acid levels, and thus arginase levels can be assessed according to the invention in any suitable biological sample. "Biological sample" as used in the context of arginine/ornithine ratio analysis is meant to include any biological sample from a patient (particularly a patient having, at risk of, or suspected of having a condition associated with elevated arginase activity), where the sample is suitable for amino acid content analysis. Exemplary biological samples include, but are not necessarily limited to blood samples (e.g., blood, serum, plasma, and other blood-derived samples), urine, cerebral spinal fluid, bronchioalveolar lavage, and the like. Amino acid levels can be assessed either quantitatively or qualitatively, usually quantitatively.

Diagnosis as to the particular type of condition having low arginine bioavailability can be made based on both an Arg/modulator(s) ratio (e.g., an Arg/(A+B) ratio (e.g., arginine/(ornithine+citrulline) ratio)) in combination with clinical signs and symptoms, generally clinical signs or symptoms that distinguish among conditions associated with elevated arginase. For example, a subject who has sickle cell disease and presents with shortness of breath, decreased exercise tolerance, and a low Arg/modulator(s) ratio (e.g., Arg/(A+B) ratio) is a candidate for diagnosis of pulmonary hypertension complicating their sickle cell disease. In contrast, a patient who presents with a low Arg/modulator(s) ratio (e.g., Arg/(A+B) ratio) and cough and/or wheeze is a candidate for diagnosis with asthma.

In another example, a patient who presents with a low Arg/modulator(s) ratio (e.g., Arg/(A+B) ratio) and has a hemolytic disorder like thalassemia is a candidate for diagnosis with pulmonary hypertension. In another example, a patient who presents with a low Arg/modulator(s) ratio (e.g., Arg/(A+B) ratio) and respiratory symptoms of shortness of breath, and/or decreased exercise tolerance that is not clinically related to asthma is a candidate for diagnosis with pulmonary hypertension and/or pulmonary fibrosis, and likely would benefit from further assessment including, for example, that includes pulmonary function tests and/or Doppler echocardiography.

In another example, a patient who presents with a low Arg/modulator(s) ratio (e.g., Arg/(A+B) ratio) and one or more of chest pain, numbness, nausea, cold sweats, numbness or weakness of the face or one or more limbs, confusion, slurred speech, dizziness, blurred vision, cardiac arrhythmia, and heart palpitations is a candidate for diagnosis with a cardiovascular disease. Cardiovascular disease includes atherosclerosis, coronary artery disease (which may result in myocardial infarction), angina, stroke, hypertension, and heart failure. For example, a patient who presents with a low Arg/modulator(s) ratio (e.g., Arg/(A+B) ratio) and chest pain may have coronary artery disease, may have had a myocardial infarction, or may be at increased risk of dying from coronary artery disease. In another example, a patient who presents with a low Arg/modulator(s) ratio (e.g., Arg/(A+B) ratio) and one or more of numbness, nausea, cold sweats, numbness or weakness of the face or one or more limbs, may have suffered a stroke or be at risk of suffering a stroke.

Other examples of clinical signs or symptoms of conditions identified herein as having decreased arginine bioavailability (e.g., due to elevated arginase activity) are well known to the ordinarily skilled artisan, and the power of the use of an Arg/modulator(s) ratio as described herein (e.g., the Arg/(A+B) ratio, such as the arginine/(ornithine+citrulline) ratio) in combination with such clinical signs and symptoms in diagnosis and differential diagnosis will be readily apparent to the skilled reader. In general, the Arg/modulator(s) ratio (e.g., Arg/(A+B) ratio) provides a tool for the clinician to guide his or her clinical suspicion.

In some settings, the Arg/modulator(s) ratio can be diagnostic where symptoms alone do not point to a definitive diagnosis. For example, with infants and small children a clinical diagnosis of asthma is difficult to make, since many kids cough or wheeze and do not have asthma. However, the Arg/modulator(s) ratio (e.g., Arg/(A+B) ratio) assessment of the present invention in combination with these symptoms allows the clinician to make a diagnosis of asthma. In providing a test for early diagnosis of asthma or other disease that might otherwise go undiagnosed, the invention avoids the situation where diagnosis is only made after repeated events of clinical signs or symptoms while the underlying cause of the symptoms goes untreated (e.g., repeated events of respiratory symptoms, while inflammation progresses untreated). In the context of asthma, an early diagnosis can avoid the situation where the untreated or maltreated patient develops airway remodeling that could have been avoided if the patient had received early anti-inflammatory treatment (e.g., inhaled steroids, oral steroids, and the like) or a treatment of the invention during the acute exacerbation.

In addition, an Arg/modulator(s) ratio that is substantially low relative to the Arg/modulator(s) ratio (e.g., Arg/(A+B) ratio) associated with an unaffected individual can indicate disease severity. A decrease in the Arg/modulator(s) ratio from an individual's baseline may also reflect disease exacerbation or progression of disease. In addition to its correlation with arginase activity, the Arg/modulator(s) ratio is a reflection of relative arginine bioavailability, and is influenced by many factors including the body's ability to compensate for low arginine levels through increased intestinal absorption of dietary arginine or increased de nova synthesis from the kidneys. These compensatory mechanisms will help maintain a more normal Arg/(A+B) ratio even when arginase activity is elevated. However, compensatory mechanisms may be affected or overwhelmed under certain conditions of disease, or progression of disease, in which case the Arg/modulator(s) ratio would decrease. A similar increase in arginase activity may have a greater impact on disease pathogenesis under conditions whereby arginine bioavailability is already compromised, e.g., as in conditions of renal dysfunction with decrease in de nova arginine synthesis.

For example, a patient who presents with an Arg/(A+B) ratio of about 0.50 or lower has or is at risk of condition of decreased arginine bioavailability (e.g., an elevated arginase condition) of a greater severity than a patient who presents with an Arg/(A+B) ratio of 0.70. In general, an Arg/(A+B) ratio that is at least 15%, 20%, or 25% less than an Arg/(A+B) ratio that is considered normal indicates the subject has or is at risk of a condition of decreased arginine bioavailability (e.g., an elevated arginase condition). Where the Arg/(A+B) ratio is an arginine/(ornithine+citrulline) ratio, a patient who presents with, for example, an arginine/(ornithine+citrulline) ratio of about 0.5, 0.4, 0.3, 0.2 or lower has or is at risk of a condition decreased arginine bioavailability (e.g., an elevated arginase condition) of a greater severity than a patient who presents with an arginine/(ornithine+citrulline) ratio of 0.6 or 0.65. In general, an arginine/(ornithine+citrulline) ratio that is at least about 75%, 80%, or 85% of an arginine/(ornithine+citrulline) ratio that is considered normal indicates the subject has or is at risk of a condition of decreased arginine bioavailability (e.g., an elevated arginase condition).

The ratios of the invention, e.g., the Arg/(A+B), Arg/(A+B+C) ratios, and particularly arginine/(ornithine+citrulline) ratios, can also be used to assess efficacy of treatment of subject having or at risk of a condition of decreased arginine bioavailability (e.g., due to elevated arginase activity), and further provides a means for rational therapy, including selection of therapy, adjustment of doses or dosage regimen, and the like. In general, therapy is indicated as being efficacious where therapy maintains or increases the arginine-to-ornithine ratio by at least about 5%, 10%, 15%, or 20% or more. In general, normalization of the ratio is a therapeutic goal or endpoint. For example, normalization of the Arg/(A+B) ratio (e.g., arginine/(ornithine+citrulline) ratio) to provide for an Arg/(A+B) ratio of greater than about 0.70 or 0.75, usually greater than about 0.8, 0.9, 1 or more is contemplated by the invention.

Additional Parameters

One or more additional parameters can be analyzed to assess disease status. For example, in the analysis of asthma patients and/or patients having or suspected of having pulmonary hypertension, additional analyses that may be performed include analysis of TH-2 cytokines, VCAM and ICAM, nitric oxide metabolite levels (in blood, breath and urine), genetic markers, IgE, sPla2 levels, respiratory syncytial virus (RSV) (e.g., in <2 year old acutely wheezing) and proteomic analysis. Nitric oxide levels in, e.g., plasma, serum, or urine, will in some embodiments be analyzed. Exhaled NO will in some embodiments be analyzed.

$NO_x$ can be measured in serum, plasma or urine using any known assay, e.g., Sievers NOAnalysis software for liquid sampling (Sievers Instruments, Inc., Denver, Colo.). See, e.g., Waugh et al. Nutritional Research 1999; 19:501-518; Meurs et al. Br J Pharmacol 2002; 136:391-398; and Morris et al. 2002. Elevated serum arginase activity in patients with sickle cell disease and pulmonary hypertension. The 30th Anniversary of the National Sickle Cell Program, Washington, D.C. As one example, serum nitrite is measured by acidifying serum to a pH<2.0 to convert nitrite to NO. Serum nitrate is measured by incubating serum with Aspergillus nitrate reductase to reduce nitrate into nitrite and then convert nitrite into NO by the addition of hydrochloric acid. The NO produced is then injected into an NO analyzer, and the NO content of the sample is determined by measuring the luminescence generated in the presence of ozone. The luminescence measured is directly proportional to the amount of NO injected and, in turn, to the nitrite and nitrate content of the samples.

Exhaled nitric oxide is measured in exhaled air, using standard methods. As one example, microprocessor-based chemiluminescent $NO_x$ analytical instrumentation is used. The test is easily performed and has been successfully used in many clinical trials. (Hamid et al. Lancet 1993; 342:1510-1513; Morris Annu Rev Nutr 2002; 22:87-105; Morris 2000. Regulation of arginine availability and its impact on NO synthesis. Nitric Oxide. Biology and Pathobiology. Academic Press, San Diego. 187-197). Subjects inhale to total lung capacity from a reservoir bag through a one-way valve (Hans Rudolph, Kansas City, Mo.) with incoming NO-free air to ensure the absence of environmental NO. Next, the subjects exhale to residual volume into the Teflon tube, which enters into the NO analyzer. The subjects exhale at a pressure of +20 mmHg into the tubing connected to the analyzer. Exhalation at this expiratory pressure without a nose clip is a maneuver that closes the velum of the posterior nasopharynx and excludes contamination by nasal NO. Secreted phospholipase A2 (sPLA2) protein is readily measured using, e.g., ELISA. sPLA2 activity is readily measured using breakdown of thioester via standard methods. See, e.g., Styles et al. Blood 1996; 87:2573-8. Serum levels of cytokines such as TNF a, sIL-2R, IL-1, IL-2, IL-4, IL-6, IL-10, g-Interferon and CD40L are readily measured using known or standard assays, e.g., commercially available ELISA kits. Similarly, levels of vascular cell adhesion molecule (VCAM), intercellular adhesion molecule (ICAM), and sCD40L are readily measured using known or standard assays, e.g., ELISA.

There are known single nucleotide polymorphisms (SNPs) in the NOS3 gene. Since NO may play a key role in the regulation of bronchomotor tone and inflammation of the airways (Li Current Opinions in Pulmon Med 1997; 3:10-16), genetic studies evaluating the NOS gene in asthmatics will in some embodiments be of interest. A method for rapidly genotyping multiple SNPs simultaneously has been developed at Roche Molecular Systems, Alameda, Calif., and involves analysis of gene products amplified by polymerase chain reaction (PCR). Exemplary PCR products that contain SNPs in genes thought to play a role in asthma include: TNFα; CCqα; TNFR1: TNFβ; IL5Rα; TNFβ; IL9; CCR2; IL4Rα; CCR5: RMS1; β2AR; CC16; FcεRIβ; CTLA4; SCYA11; IL4Rα; IL4; and IL6.

Computer Programs and Systems

Calculation of the Arg/modulator(s) ratio and comparison to a normal Arg/modulator(s) ratio can be performed manually. Alternatively, calculation of the levels of arginine and modulators of arginine bioavailability (e.g., citrulline, ornithine, and the like) and diagnosis of a ratio as being normal, borderline or below normal can be partially or fully automated, e.g., using a computer-based system.

For example, the levels of arginine, a first modulator of arginine bioavailability and a second modulator of arginine bioavailability can be can be entered into a programmed computer, where these data can be entered manually or directly from a device which measures these amino acid levels. The programmed computer then calculates the desired Arg/modulator(s) ratio (e.g., the Arg/ornithine ratio; the Arg/citrulline ratio; the Arg/(A+B) ratio (e.g., arginine/(ornithine+citrulline) ratio); the Arg/(A+B+C) ratio, and the like)) and, optionally, compares the selected ratio to a normal ratio.

Where the program determines the calculated ratio is at least equal to or greater than a normal ratio (also referred to as a normal threshold value), the computer then provides a read out indicating the patient has a normal Arg/modulator(s) ratio. Where the program determines the Arg/modulator(s) ratio is at less than or equal to a normal threshold value (e.g., for Arg/(A+B), less than or equal to about 0.7) but greater than a threshold value associated with a disease threshold value (e.g., for Arg/(A+B), greater than about 0.7), then the computer then provides a read out indicating the patient has a borderline Arg/(A+B) ratio and is at risk of developing a condition having elevated arginase activity. Finally, where the program determines the ratio is less than a disease threshold value (e.g., for Arg/(A+B) ratio is less than about 0.7), then computer then provides a read out indicating the patient has an abnormally low ratio, and the patient has or is at risk of developing a condition of decreased arginine bioavailability (e.g., due to elevated arginase activity).

Associated programming for carrying out the computer-based methods of the invention can be recorded on computer readable media (i.e., any medium that can be read and accessed by a computer). Such media include, but are not limited to: magnetic storage media, such as floppy discs, hard disc storage medium, and magnetic tape; optical storage media such as CD-ROMs and DVDs; electrical storage media such as RAM, ROM and EPROM; and hybrids of these categories such as magnetic/optical storage media.

In one embodiment, the programming for carrying out analysis of an Arg/modulator(s) ratio according to the invention is provided in computer-based system. As used herein, "a computer-based system" refers to a suitable combination of, based on the method to be carried out and how the program is to be provided, a software element, a data storage element, and, optionally, a hardware element, and an output element. The software element provides the programming that, when implemented on a computer, provides for calculation of an Arg/modulator(s) ratio (e.g., an Arg/(A+B) ratio (e.g., arginine/(ornithine+citrulline) ratio and/or other amino acid ratios)) and, optionally, comparing the calculated Arg/modulator(s) ratio to a value of a normal Arg/modulator(s) ratio (e.g., a normal Arg/(A+B) ratio) to provide a diagnosis. The data storage element can provide for storage of the program, and optionally storage of data involved in calculating the ratio as well as the result of such calculation. The hardware element provides the means for executing the program, while the display element allows for display of the analysis, particularly the result, to the user. The minimum hardware of the computer-based system generally comprises a central processing unit (CPU), input element, output element, and data storage element. A skilled artisan can readily appreciate that any one of the currently available computer-based system can be programmed to implement the method of the invention, and are suitable for use in the present invention. The data storage element can comprise any manufacture comprising a recording of the present sequence information as described above, or a memory access means that can access such a manufacture.

Figure 5:
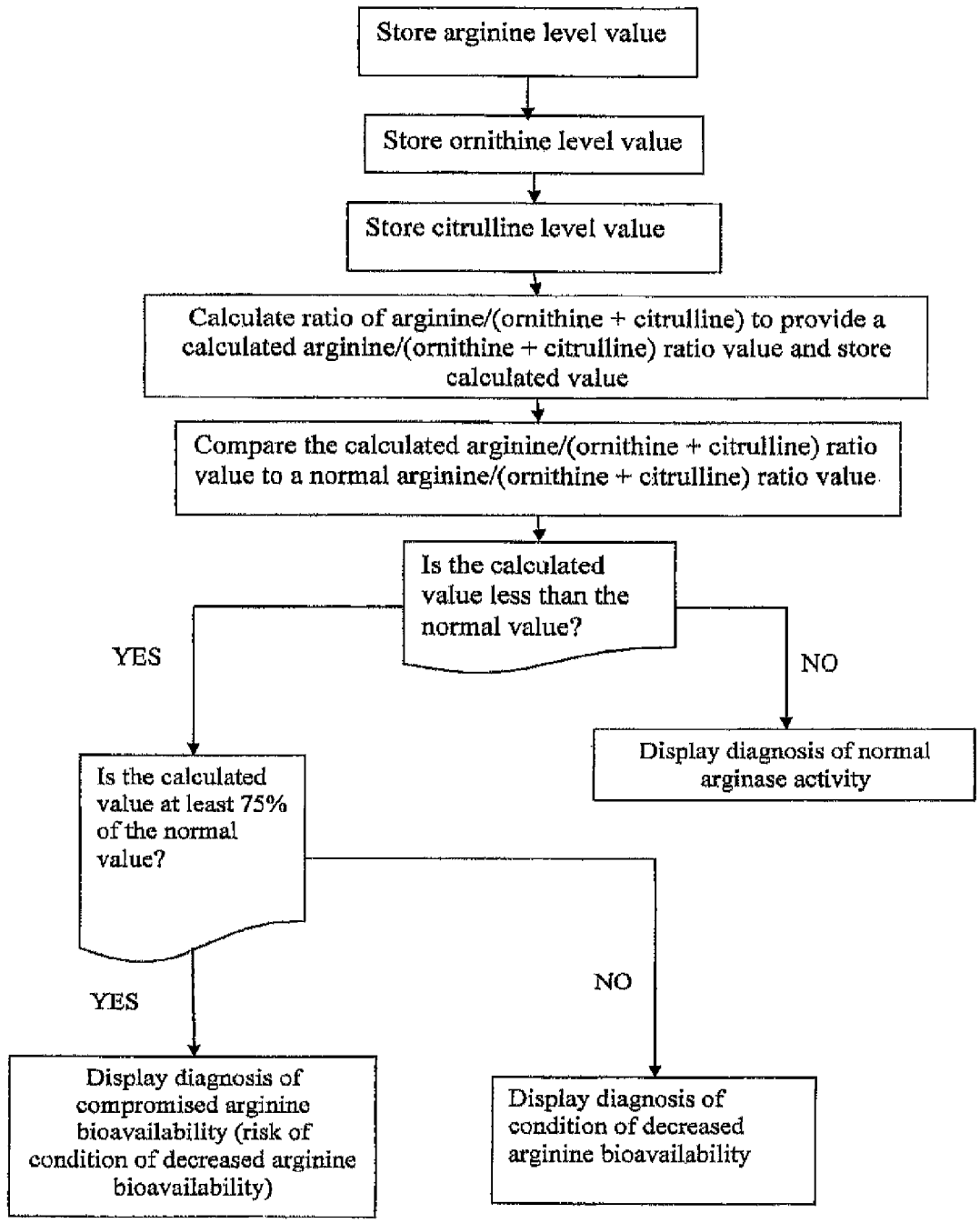
FIG. 5 is an exemplary flowchart of a computer program for assessing the ratio of arginine/(ornithine+citrulline).

FIG. 5 is an exemplary flowchart of a computer program for assessing an Arg/modulator(s) ratio, here exemplified by an arginine/(ornithine+citrulline) ratio. In this example, an arginine level value is stored, a citrulline level is stored, and an ornithine level value is stored. It is noted that the order in which these values are stored as indicated in FIG. 5 is not meant to be limiting. Although not shown in this example, the arginine, citrulline, and/or ornithine level values are obtained from a sample by a device, which may provide these values for manual entry, or which may provide for automated transfer of the values to the program described herein.

As exemplified in FIG. 5, the ratio of arginine/(ornithine+citrulline) ratio is calculated by dividing the arginine level value by the sum of the ornithine level value and the citrulline level value to provide a calculated arginine/(ornithine+citrulline) ratio value. The calculated value is then compared to a normal arginine/(ornithine+citrulline) ratio value. If the calculated value is not less than the normal value, then a diagnosis of normal arginine bioavailability is made. As illustrated in FIG. 5, this diagnosis can be displayed to the user. If the calculated value is less than the normal value, then the program queries whether the calculated value is at least 95%, 90%, 85%, 80%, or 75% of the normal value (with at least 75% of normal exemplified in FIG. 5. If yes, then a diagnosis of compromised arginine bioavailability is displayed to the user, which may optionally also display a diagnosis of risk of decreased arginine bioavailability. Where the calculated value of the Arg/modulator(s) ratio is not equal to or greater than normal but is at least, for example, 75% of the value of the normal Arg/modulator(s) ratio, then a diagnosis of at risk for low arginine bioavailability is displayed to the user (e.g., arginine bioavailability is not so low as to provide a diagnosis of an existing condition of decreased arginine bioavailability, but the patient is at risk of developing such a condition). If the Arg/modulator(s) ratio value is not at least 75% of a normal Arg/modulator(s) ratio value (i.e., the Arg/modulator(s) ratio value is at least 25% less than an normal Arg/modulator(s) ratio value), then a diagnosis of a condition of decreased arginine bioavailability (e.g., due to elevated arginase activity) is displayed to the user.

In another embodiment, the calculated Arg/modulator(s) ratio value, exemplified by the arginine/(ornithine+citrulline) ratio value, is simply displayed, with the further steps illustrated in FIG. 5 being optional. In another embodiment, the program is modified so as to provide a display that reflects efficacy of a therapy which the patient is receiving. For example, if the calculated Arg/modulator(s) ratio value (e.g., arginine/(ornithine+citrulline) ratio value) is not less than the normal value, then the display can indicate that therapy is efficacious or that arginine bioavailability has normalized. As illustrated in this example in FIG. 5, if the calculated arginine/(ornithine+citrulline) ratio is not a normal value, but is at least about 75% of the nominal value, then the display can indicate that low arginine bioavailability persists and/or modification or termination of current therapy is advised. If the calculated value is not at least about 75% of the nominal value, then a display indicating partial or possible efficacy and that modification of therapy (e.g., adjustment of dose or dosage regimen) may be indicated.

Assessing Therapy

The methods of the invention can be used to monitor therapy. For example, following administration of a therapy according to the invention, efficacy can be assessed in the patient by, assessing arginine bioavailability, e.g., by assessing normalization of an Arg/modulator(s) ratio as described herein. Doses of agents administered can be adjusted in accordance to patient need, e.g., to provide for an increase in an Arg/modulator(s) ratio as described herein, and thus an increase in arginine bioavailability, to within a normal range, e.g., within a range such that arginase levels are not above normal levels more than about 5%, 10%, 15%, or 20%, or a sufficient increase in plasma arginine concentration to the extent that arginine bioavailability is no longer limiting factor for nitric oxide production, i.e., levels above the Km for arginine transport (>120 µM), and a normalization of the arginine-to-ornithine ratio (e.g., >1.5).

Therapy can also be assessed by examining improvement in one or more clinical symptoms of disease. Successful therapy is normally considered to be a significant improvement in one or more clinical symptoms after treatment according to the invention as compared to prior to such treatment, e.g., improvement in one or more clinical parameters of the condition by at least about 10%, at least about 15%, at least about 25%, at least about 50%, or more, compared to the clinical parameter prior to therapy, or compared with a placebo control or an untreated control. For example, in pulmonary hypertension, clinical parameters assessed can be one or more of: an improvement in mean pulmonary artery systolic pressure as estimated by tricuspid regurgitant jet velocity measured by Doppler-echocardiography, improved exercise tolerance as measured by a "6-minute walk"; blood pressure in systemic hypertension, etc).

In the context of conditions that affect lung function, the clinical parameters can be, for example, forced inspiratory flow (FIF), forced expiratory flow (FEF), forced vital capacity (FVC), diffusing capacity for carbon monoxide (DLco), and/or the like. For example, in asthma, therapy can be assessed by spirometry, lung volume, airway resistance, and/or oxygen saturation, as well as improvements in clinical symptoms such as cough, wheeze, night-time wake-ups due to cough or respiratory problems, decreased need for rescue-med usage such as albuterol, and the like. In patients having pulmonary hypertension, therapy can be assessed using lung function tests, as well as assessing mean pulmonary artery pressure (e.g., at rest and/or with exercise). It should be noted that successful therapy according to the invention includes outcomes where the underlying disease state is not significantly altered, but one or more clinical symptoms (including symptoms that arise from or are associated with the disease) are treated.

In the context of sickle cell disease, clinical parameters include, for example one or more of: a decrease in the number of pain crisis, number emergency department visits, number of hospitalizations and/or duration of hospitalization, amount of pain medication use, incidence of and/or occurrence of complications such as skin ulcers, need for transfusion, oxygen use, etc. Also improved pain scores and quality of life assessment tools can be followed.

In the context of cardiovascular disease, clinical parameters include, e.g., one or more of: decrease in the number or incidence of chest pain; decrease in the number or incidence of symptoms of stroke, e.g., numbness of face and/or limb(s), blurred vision, dizziness, etc.; decrease in mortality; and improved cardiovascular function (e.g., as assessed by electrocardiogram, etc.).

The Arg/modulator(s) ratio can provide guidance to the practitioner to adjust therapy. Such adjustments can include adjustment to a dosage regimen (e.g., increasing or decreasing dose of a therapeutic agent, increasing or decrease frequency of dose, and the like), or switching the patient to a different therapy. The therapy can involve any suitable therapeutic agent, such as L-arginine monotherapy, arginase inhibitor for monotherapy, L-Arg and arginase inhibitor combination therapy, combination therapies involving magnesium, or other therapy (see, e.g., WO 2004/073623).

Kits

The invention also provides kits having components and instructions for use in assessing levels of arginine and modulators of arginine bioavailability (e.g., ornithine levels, citrulline levels, proline levels creatine levels, methylated arginines, and the like) in a subject. In one embodiment, the kit includes a chart to facilitate calculation of Arg/modulator(s) ratio of the invention (e.g., the Arg/(A+B) ratio) and/or for assessing whether the Arg/modulator(s) ratio is normal, borderline, or indicative of a condition of decreased arginine bioavailability. In another embodiment, the kit includes a handheld device which is preprogrammed to receive the values of the levels of arginine and arginine bioavailability modulators (e.g., citrulline, and ornithine), calculate an Arg/modulator(s) ratio (e.g., the Arg/(A+B) ratio) and, optionally, provide a readout indicating whether the calculated Arg/modulator(s) ratio is normal, borderline, or low as described above. The device can also optionally provide a diagnosis of normal, at risk, or having a condition of decreased arginine bioavailability. In another embodiment, the kit includes the materials necessary to determine, e.g., measure, the quantitative levels of arginine and arginine bioavailability modulators (e.g., citrulline, and ornithine) from the sample provided.

Kits can optionally include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the interne, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Analysis of Amino Acid Levels in Asthmatics, Sickle Cell Disease, and PHT Patients Methods and Materials Asthma patients. Patients with asthma presenting to the emergency department and clinics at Children's Hospital and Research Center at Oakland were recruited. Blood samples and exhaled nitric oxide levels (in patients old enough to perform peak flow) are obtained at presentation to the emergency department or clinic, and followed daily during hospitalization for those patients ill enough to require admission.

Baseline blood was obtained at least 4 weeks after resolution of the acute exacerbation. Blood samples were analyzed for arginine and amino acid levels, arginase activity, and arginine-to-ornithine ratio.

Sickle cell patients. Seventeen sickle cell disease patients with documented pulmonary hypertension at steady-state were enrolled in the study. All known patients with pulmonary hypertension receiving care at the Northern California Comprehensive Sickle Cell Center were approached for participation in this analysis. Twelve patients were homozygous for hemoglobin S, three patients had hemoglobin type SC, and two patient had hemoglobin Sβ-thalassemia. The mean age of patients was 32.7±15 years with a range of 13 to 63 years. There were seven women enrolled. Ten ethnically matched normal non-sickle cell disease volunteers were enrolled as a control group in order to compare amino acid levels and arginase activity. The mean age was 20.6±10 years, ranging from 10 to 34 years. There were four females and six males enrolled. Pulmonary hypertension was defined as estimated pulmonary artery pressures>30 mm Hg by echocardiogram (or tricuspid regurgitant jet velocity of greater than 2.5 m/sec), >two months duration, not associated with acute chest syndrome. A chart review was performed on all patients to obtain tricuspid regurgitant jet velocity data from previous echocardiograms.

Amino Acid Levels. (A complete amino acid panel, including arginine, citrulline, ornithine, and L-arginine analogue asymmetric di-methyl-L-arginine). Quantitative plasma amino acid levels were measured in µmmol/L, using a Beckman 6300 amino acid analyzer. The amino acids were separated on an lithium ion exchange column and then reacted with ninhydrin to generate a color response. The data are collected and analyzed using Beckman 32 Karat software, at the Molecular Structure Facility, University of California, Davis, Calif.

Arginase: Arginase-specific activity was determined in plasma by methods previously described. (Morris et al. Am J Physiol Endocrinol Metab 1998; 275:740-747).

Results

Reductions were seen in plasma levels of many amino acids in asthmatic patient experiencing an acute exacerbation of respiratory symptoms (Table 1). Strikingly, the greatest decrease was in plasma levels of arginine, which were approximately half those of normal controls (45±22 µM vs. 94±29 µM; $p<0.0001$).

TABLE 1

Plasma Amino Acids in Normal Controls vs. Asthma

| Amino Acid | Concentration (µM) | | % Control | p-value |
|---|---|---|---|---|
| | Controls (n = 15) | Asthma (n = 26) | | |
| Arginine | 94 ± 29 | 45 ± 22 | 48 | <0.0001 |
| Ornithine | 64 ± 21 | 49 ± 24 | 77 | NS |
| Citrulline | 30 ± 6 | 21 ± 10 | 70 | 0.002 |
| Proline | 195 ± 66 | 144 ± 73 | 74 | 0.03 |
| Hydroxyproline | 29 ± 14 | 19 ± 9 | 66 | 0.02 |
| Lysine | 162 ± 33 | 112 ± 57 | 69 | 0.004 |
| Glutamic Acid | 55 ± 29 | 40 ± 16 | 73 | 0.04 |
| Glutamine | 554 ± 86 | 466 ± 148 | 84 | 0.04 |
| Glycine | 251 ± 64 | 186 ± 103 | 74 | 0.03 |
| Alanine | 369 ± 104 | 292 ± 96 | 79 | 0.02 |
| Valine | 223 ± 52 | 161 ± 51 | 72 | <0.001 |
| Aspartic Acid | 9 ± 6 | 7 ± 1 | 78 | 0.04 |
| Threonine | 136 ± 29 | 99 ± 58 | 73 | 0.02 |
| Isoleucine | 66 ± 20 | 48 ± 23 | 73 | 0.01 |
| Leucine | 126 ± 32 | 96 ± 45 | 76 | 0.03 |
| Tyrosine | 72 ± 15 | 52 ± 20 | 72 | 0.002 |
| Histidine | 75 ± 10 | 57 ± 20 | 79 | 0.003 |
| Cysteine | 22 ± 13 | 20 ± 16 | 90 | NS |
| Asparagine | 35 ± 15 | 41 ± 18 (n = 25) | 118 | NS |
| Serine | 107 ± 32 | 89 ± 64 | 83 | NS |
| Tryptophan | 45 ± 10 | 37 ± 15 | 82 | NS |
| Methionine | 25 ± 6 | 20 ± 13 | 80 | NS |
| Phenylalanine | 57 ± 13 | 56 ± 17 | 98 | NS |

Concentrations of amino acids are expressed as means ± SD. % Control values reflect percentages of controls for the asthma group.

As arginine, ornithine and lysine are taken up by cells via the same transport system, the ratio arginine/(ornithine+lysine) provides an index of relative arginine availability at any given plasma arginine concentration. Relative arginine availability also was significantly lower in asthmatic patients as compared to normal controls (0.30±0.13 vs. 0.42±0.14, p<0.005), further limiting arginine availability in the asthma group. Asthma in the subject was accompanied by a decreased Arg/ornithine+citrulline ratio compared to non-asthmatic controls.

Plasma levels of ornithine (Table 1), a product of arginine catabolism, were generally lower in asthmatics relative to controls, and relative ornithine availability (ornithine/(arginine+lysine)) was somewhat higher in asthmatics than in controls (0.25±0.07 for controls, 0.34±0.17 for asthma), but neither of these trends reached statistical significance. On the other hand, citrulline, the precursor of endogenous arginine synthesis, was significantly reduced in asthmatics relative to normal controls (Table 1), possibly contributing to the decrease in plasma arginine levels in these patients.

Table 2 shows plasma amino acids in normal controls vs. patients with sickle cell disease (SCD). An abnormal amino acid profile is found in patients with sickle cell disease. The greatest deficiency is found in plasma arginine concentration. SCD in the subject was accompanied by a decreased Arg/ornithine+citrulline ratio compared to non-asthmatic controls.

TABLE 2

Plasma Amino Acids in Normal Controls vs. SCD

| Amino Acid | Concentration (µM) | | % Control | p-value |
|---|---|---|---|---|
| | Controls (n = 29) | SCD (n = 163) | | |
| Nonessential: | | | | |
| Arginine | 65 ± 16 | 40 ± 15 | 62 | <0.0001 |
| *Ornithine | 61 ± 22 | 64 ± 23 | — | NS |
| *Citrulline | 27 ± 11 | 25 ± 14 | — | NS |
| *Proline | 141 ± 49 | 205 ± 76 | 145 | <0.0001 |
| *Glutamic acid | 38 ± 15 | 47 ± 24 | 124 | 0.04 |
| Glutamine | 515 ± 129 | 607 ± 125 | 118 | 0.0004 |
| Glycine | 205 ± 48 | 278 ± 98 | 136 | 0.0001 |
| Tyrosine | 61 ± 13 | 53 ± 19 | 87 | 0.03 |
| Alanine | 330 ± 69 | 321 ± 110 | — | NS |
| *Cysteine | 40 ± 7 | 45 ± 15 | — | NS |
| Serine | 93 ± 15 | 94 ± 23 | — | NS |

TABLE 2-continued

Plasma Amino Acids in Normal Controls vs. SCD

| Amino Acid | Concentration (μM) | | % Control | p-value |
|---|---|---|---|---|
| | Controls (n = 29) | SCD (n = 163) | | |
| Asparagine | 44 ± 13 | 43 ± 14 | — | NS |
| Essential: | | | | |
| Lysine | 161 ± 30 | 143 ± 34 | 89 | 0.006 |
| Histidine | 73 ± 15 | 56 ± 16 | 77 | <0.0001 |
| Phenylalanine | 61 ± 13 | 53 ± 19 | 87 | 0.03 |
| *Leucine | 114 ± 25 | 89 ± 28 | 78 | <0.0001 |
| *Valine | 207 ± 41 | 162 ± 45 | 78 | <0.0001 |
| Isoleucine | 58 ± 13 | 49 ± 16 | 84 | 0.008 |
| Methionine | 25 ± 5 | 26 ± 7 | — | NS |
| Threonine | 137 ± 31 | 126 ± 45 | — | NS |

Concentrations of amino acids are expressed as means ± SD.
% Control: Values are shown only when significantly different from controls.
*Amino acids that are altered in SCD patients with PHT vs. SCD patients without PHT Table 3 illustrates plasma amino acid levels that differ in sickle cell disease patients with pulmonary hypertension compared to those without pulmonary hypertension. Elevated downstream by-products of arginase activity occur in SCD patients who have developed pulmonary hypertension.

TABLE 3

Plasma Amino Acids in SCD without PHT vs. SCD with PHT

| Amino Acid | Concentration (μM) | | | p-value |
|---|---|---|---|---|
| | Controls (n = 29) | TR jet < 2.5 (n = 86) | TR jet ≥ 2.5 (n = 41) | (PHT vs non PHT) |
| Nonessential: | | | | |
| Ornithine | 61 ± 22 | 59 ± 20 | 69 ± 23 | 0.02 (↑) |
| Citrulline | 27 ± 11 | *22 ± 10 | 29 ± 20 | 0.008 (↑) |
| Proline | 141 ± 49 | *192 ± 74 | *236 ± 87 | 0.003 (↑) |
| Glutamic acid | 38 ± 15 | *45 ± 16 | *60 ± 37 | 0.003 (↑) |
| Cysteine | 40 ± 7 | 43 ± 14 | *48 ± 16 | 0.04 (↑) |
| Essential: | | | | |
| Valine | 207 ± 41 | *165 ± 41 | *145 ± 48 | 0.01 (↓) |
| Leucine | 114 ± 25 | *92 ± 25 | *78 ± 30 | 0.006 (↓) |

Concentrations of amino acids are expressed as means ± SD.
*Amino acids that differ significantly (p < 0.05) from controls Including citrulline in the Arg/modulator(s) ratio, e.g., to calculate the Arg/ornithine+citrulline ratio, takes into consideration the impact of renal insufficiency on de novo arginine synthesis in addition to the impact of elevated arginase activity on arginine catabolism, an thus is a superior reflection of global arginine bioavailability. In addition to its association with asthma and sickle cell disease, the Arg/ornithine+citrulline ratio is associated with pulmonary hypertension in both sickle cell disease, primary pulmonary hypertension and in pulmonary artery hypertension associated with collagen vascular disease. In addition, the Arg/ornithine+citrulline ratio represents an independent risk factor for mortality in sickle cell disease (risk ratio: 3.4, [1.5, 7.7], p<0.001).

Example 2

Decreased Arginine Bioavailability Contributes to the Pathogenesis of Pulmonary Arterial Hypertension Alterations in amino acid metabolism occurring in pulmonary artery hypertension (PAH) that could be impacted by elevated arginase activity were investigated. Plasma amino acids were determined in normal (NL) controls and patients diagnosed with primary pulmonary hypertension (PH) or PAH associated with scleroderma or systemic lupus erythematosis. These data are provided in Table 4 below.

TABLE 4

| Variable | NL Control (n = 36) | PAH (n = 20) | P* |
|---|---|---|---|
| Arginine (μM) | 67 ± 18 | 50 ± 15 | <0.01 |
| Ornithine (μM) | 62 ± 22 | 102 ± 30 | <0.001 |
| Arg/Orn ratio | 1.2 ± 0.5 | 0.6 ± 0.4 | <0.001 |
| Glutamic acid (μM) | 38 ± 15 | 127 ± 75 | <0.001 |
| Proline (μM) | 161 ± 48 | 202 ± 65 | <0.01 |
| Citrulline (μM) | 25 ± 11 | 38 ± 14 | <0.001 |

Plasma Arg levels were low, Orn levels were high, and the Arg-to-Orn ratio was low in PAH as compared to normal controls. Consistent with a shift in Arg metabolism away from NO production and towards the ornithine-dependent pathways, both glutamic acid and proline levels were elevated in PAH. Citrulline levels were also high in PAH. Since Arg is produced from citrulline in the kidneys, renal dysfunction may also contribute to decreased Arg bioavailability. The Arg/[Orn+Citrulline] ratio correlated with mean pulmonary artery pressure (PAP) measured on cardiac catheterization (r=−0.68, p<0.01), since it incorporates the impact of arginase activity and renal impairment.

Decreased Arg bioavailability and a shift of metabolism towards ornithine-dependent pathways are play a role in PAH, again supporting the use of therapies that maximize Arg and NO bioavailability in treatment of such conditions.

Example 3

Decreased Arginine Bioavailability and Elevated Arginase Activity in Thalassemia Data on the levels of amino acids and arginase activity in plasma samples obtained from thalassemia ("thal") patients was collected (8 thal-major, 4 E-beta thal, 2 Hb H alpha thal). All but 3 patients were on chronic transfusion therapy. Echo results were available on 9 patients and demonstrated 6/9 with a tricuspid regurgitant jet velocity≧2.5 m/s. The data are provided in Table 5.

TABLE 5

| Variable | NL Control (n = 36) | Thalassemia (n = 14) | p* |
|---|---|---|---|
| Arginine (μM) | 67 ± 18 | 57 ± 26 (50) | 0.15 |
| Ornithine (μM) | 62 ± 22 | 85 ± 68 | 0.05 |
| Arg/Orn ratio | 1.2 ± 0.5 | 0.79 ± 0.4 | <0.01 |
| Arg/Orn + Cit | 0.82 ± .27 | 0.50 ± .4 | <0.01 |
| Proline (μM) | 161 ± 48 | 258 ± 116 | <0.001 |
| Citrulline (μM) | 25 ± 11 | 42 ± 17 | <0.001 |
| Arginase (μmol/cc/hr) | 0.33 ± 0.2 (n = 45) | 0.71 ± 0.3 | <0.001 |

Plasma arginine concentration trended lower in patients with thalassemia, with values ranging from normal to very low (19.5 to 122 μM, median 50 μM). Ornithine levels were high, and the arginine-to-ornithine ratio low in thalassemia patients. Plasma arginase activity was significantly elevated, although a range of values is observed (0.06-1.17 μmol/cc/hr, median 0.83 μmol/cc/hr). Proline was also elevated, a downstream metabolite of arginase activity and likely a contributor to pulmonary vascular remodeling. Of interest, exhaled nitric oxide levels were also significantly elevated in thalassemia (49±41 parts per billion vs. 18±8 ppb, p=0.02 thal vs. normal controls), suggesting an upregulation of nitric oxide synthase in the lungs of patients with thalassemia in addition to higher plasma arginase activity.

These data indicate that the Arg:Orn+citrulline ratio is an indicator of disease in thalassemia, and further that thalassemia patients are candidates for therapy according to the invention.

Example 4

Arginase Activity in Sickle Cell Disease

The goal of this study was to identify the source of increased plasma arginase activity in a large cohort of patients with sickle cell disease and to evaluate the contribution of dysregulated arginine metabolism to patient morbidity.

Patients. The patient population was comprised of 228 sequentially enrolled subjects with sickle cell disease hemoglobinopathies and includes a subset of 195 subjects that has been described in detail (Gladwin et al. *N Engl J Med.* 2004; 350:22-31). Informed consent was signed by each subject for an institutional review board-approved protocol to obtain clinical information, echocardiography, blood specimens and prospective clinical follow-up data for research analysis. Detailed patient characteristics are shown in Table 6.

TABLE 6

Characteristics of the sickle cell disease study population.

| Patient characteristic* | SCD* | n | Controls | n | p |
|---|---|---|---|---|---|
| Age (years) | 36 ± 11 | 228 | 37 ± 11 | 36 | .68 |
| Alanine aminotransferase (U/L) | 27 ± 15 | 225 | 23 ± 12 | 36 | .14 |
| Albumin (mg/dL) | 4.1 ± 0.4 | 224 | 4.1 ± 0.2 | 35 | .29 |
| Alkaline phosphatase (U/L) | 115 ± 87 | 224 | 78 ± 23 | 36 | .004 |
| Aspartate aminotransferase (U/L) | 41 ± 22 | 223 | 23 ± 8 | 36 | <.001 |
| Blood urea nitrogen (mg/dL) | 10 ± 10 | 225 | 12 ± 4 | 36 | .002 |
| C-reactive protein (μg/mL) | .57 ± .91 | 203 | .35 ± 0.46 | 35 | .04 |
| Creatinine (mg/dL) | .71 (.67, .76) | 225 | .88 (.80, .96) | 36 | .02 |
| Erythrocyte sedimentation rate (mm/hr) | 39 ± 31 | 180 | 21 ± 18 | 35 | <.001 |
| Gender (% female) | 60 | 228 | 53 | 36 | .44 |
| Hematocrit (%) | 28 ± 5 | 226 | 41 ± 4 | 36 | <.001 |
| Haemoglobin (g/dL) | 9.5 ± 1.8 | 226 | 13.7 ± 1.5 | 36 | <.001 |
| Haemoglobin F (%) | 7.4 ± 6.6 | 227 | .4 ± .6 | 33 | <.001 |
| Haemoglobin SC (%) | 18 | 228 | | | |
| Lactate dehydrogenase (U/L) | 347 ± 158 | 204 | 166 ± 39 | 35 | <.001 |
| Reticulocyte count (per uL) | 243 ± 132 | 214 | 66 ± 28 | 33 | <.001 |
| Tricuspid regurgitant jet velocity (m/sec) | 2.3 ± 0.6 | 224 | 1.9 ± .5 | 36 | .002 |
| Triglycerides (mg/dL) | 116 ± 68 | 200 | 79 ± 49 | 29 | <.001 |
| Weight (kg) | 71 ± 18 | 178 | 87 ± 53 | 33 | <.001 |
| White blood cell count (thousand/uL) | 10.2 ± 3.7 | 226 | 5.7 ± 2 | 36 | <.001 |

*Mean ± standard deviation for continuous variables (except creatinine, for which geometric mean and 95% confidence interval are shown because of extremely high values in SCD patients); percentage with characteristic for dichotomous variable.
**From two-sided t-test for continuous variables (on log10 transformed values for laboratory assays); chi-square test without continuity correction for dichotomous variables.

In this population of patients with sickle cell disease, right heart catheterization studies have confirmed that a tricuspid regurgitant jet velocity<2.5 meters/second corresponds to normal pulmonary artery pressures, tricuspid regurgitant jet velocity 2.5-2.9 meters/second corresponds to mild pulmonary hypertension, and tricuspid regurgitant jet velocity>2.9 meters/second corresponds to moderate/severe pulmonary hypertension (Gladwin et al. *N Engl J Med.* 2004; 350:22-31). Pulmonary hypertension was prospectively defined as a tricuspid regurgitant jet velocity≧2.5 meters/second on Doppler-echocardiography. Additionally, 45 matched African-American control subjects, similar to the sickle cell patients in age and gender distributions, were evaluated for race-based comparisons of laboratory and echocardiographic data.

Amino Acid Measurement. Plasma amino acids were quantified via ion exchange chromatography (Beckman model 6300 amino acid analyzer, Fullterton, Calif.) at the Mayo Clinic, Rochester Minn. by methods recommended by the manufacturer.

Arginase activity. Arginase activity, consecutively obtained in the first 140 patients participating in the study, was determined as the conversion of [$^{14}$C-guanidino]-L-arginine to [$^{14}$C]urea, which was converted to $^{14}CO_2$ by urease and trapped as $Na_2{}^{14}CO_3$ for scintillation counting as previously described (Morris et al. *Am J Physiol.* 1998; 275:E740-747). Briefly, aliquots of plasma or red blood cell-lysate were spun down upon collection and frozen at −80° Celsius. Samples were later incubated for 10 min at 55° C. in complete assay mixture lacking arginine. The reaction was initiated by addition of labeled arginine and incubation was continued at 37° Celsius for 2 hours. The reaction was terminated by heating at 100° Celsius for 3 minutes. Samples were incubated with urease at 37° Celsius for 45 minutes, and $Na_2{}^{14}CO_3$ was trapped on NaOH-soaked filters following acidification of the samples with HCl to volatilize the $^{14}CO_2$.

Enzyme-Linked Immunosorbent Assay (ELISA). Plasma levels of sVCAM-1, sICAM-1, sE-selectin, and sP-selectin were measured using commercially available ELISA kits (R&D Systems, Minneapolis, Minn.).

Measurement of Myeloperoxidase levels. Myeloperoxidase levels were measured with use of an enzyme-linked immunosorbent assay (PrognostiX, Cleveland, Ohio). Each plate included a standard curve with isolated myeloperoxidase (extinction coefficient of 178,000 $M^{-1}cm^{-1}$) and controls to correct for interplate variability.

Data Analysis. Data were collected for patients with all genotypes of sickle cell disease. Descriptive statistics presented are mean±standard deviation, geometric mean and 95% confidence interval (CI), or percentage with characteristic, as appropriate. Two-sided t-tests were used to compare amino acid values in sickle cell patients and normal controls. Linear regression was used to evaluate relationships between amino acid values and tricuspid regurgitant jet velocity. Since normal distributions provided poor approximations for many of the variables of interest, bivariate associations were assessed using the Spearman rank correlation coefficient. Multiple regression analysis of arginase activity used $log_{10}$-transformed values for arginase, as well as for laboratory correlates for which logarithms were better fit than untransformed values by normal distributions. Proportional hazards (Cox) regression was used to study relationships between mortality in sickle cell patients and covariates of interest. P-values<0.05 were considered statistically significant. Analysis was done using NCSS software (Number Cruncher Statistical Systems, Kaysville, Utah).

Plasma Amino Acid Levels

Plasma amino acid levels in sickle cell disease patients were compared to ethnically matched control subjects without sickle cell disease (Table 7).

TABLE 7

Distribution (mean ± standard deviation) of amino acids linked to the
L-arginine-nitric oxide pathway in sickle cell disease patients with tricuspid regurgitant jet
velocity (TRV) <2.5 m/s, 2.5-2.9 m/s, and ≧3.0 m/s, and in normal controls.

| Variable | NL Control (n = 36) | All SCD (n = 209) | p* | TRV < 2.5 (n = 131) | 2.5-2.9 (n = 53) | TRV ≧ 3.0 (n = 21) | p** |
|---|---|---|---|---|---|---|---|
| Arginine | 67 ± 18 | 41 ± 16 | <.001 | 41 ± 16 | 41 ± 15 | 39 ± 15 | 0.51 |
| Ornithine | 62 ± 22 | 65 ± 23 | .38 | 63 ± 21 | 65 ± 25 | 81 ± 24 | 0.003 |
| Proline | 154 ± 48 | 210 ± 75 | <.001 | 202 ± 70 | 219 ± 80 | 245 ± 88 | 0.01 |
| Citrulline | 25 ± 11 | 25 ± 13 | .85 | 23 ± 12 | 26 ± 15 | 27 ± 14 | 0.09 |
| Arg/Orn | 1.2 ± .5 | 0.71 ± .4 | <.001 | 0.74 ± .4 | 0.72 ± .4 | 0.49 ± .2 | 0.03 |
| Arg/(Orn + Cit) | 0.82 ± .3 | 0.5 ± .3 | <.001 | 0.53 ± .3 | 0.50 ± .3 | 0.36 ± .1 | 0.02 |

*From two-sided two-sample t-test
**From linear regression (using $\log_{10}$-transformed values) on level of TRV, coded 0, 1, 2

An abnormal amino acid profile was observed in patients with sickle cell disease that is consistent with altered arginine metabolism. The observed dysregulation of the arginine-to-nitric oxide metabolism was greatest in sickle cell disease patients with pulmonary hypertension. Although plasma arginine concentrations were low in sickle cell disease compared to normal controls, these levels were similar in patients with and without pulmonary hypertension. However, plasma ornithine levels were higher in sickle cell patients with pulmonary hypertension vs. sickle cell disease patients without pulmonary hypertension, suggestive of elevated arginase activity. The arginine-to-ornithine ratio, an indirect measure of arginase activity and relative arginine bioavailability, was low in patients with sickle cell disease compared to normal controls ($p<0.0001$; FIG. 1, Panel A), and correlated with tricuspid regurgitant jet velocity, a non-invasive measure of pulmonary artery systolic pressure ($r=-0.21$, $p=0.001$). A significant relationship also emerges from linear regressions analysis done on the three categories of tricuspid regurgitant jet velocity (<2.5, 2.5-2.9, and ≧3.0 meters/second), revealing a correlation of arginine-to-ornithine ratio with severity of pulmonary hypertension ($p=0.03$; FIG. 1, Panel B).

Plasma proline concentrations were also significantly increased, possibly indicating increased conversion of ornithine to proline in sickle cell disease that is amplified in patients with pulmonary hypertension (Table 7). Highest proline levels occurred in patients with moderate/severe pulmonary hypertension ($p=0.01$). Citrulline levels also trended higher in patients with pulmonary hypertension and correlated with rising creatinine levels ($r=0.54$, $p<0.0001$), consistent with impaired renal function. In aggregate these data indicate significant modulation of L-arginine metabolism in sickle cell disease that is associated with the development of pulmonary and renal vasculopathy.

Arginase Activity in Plasma. In order to understand the mechanism responsible for dysregulation of L-arginine metabolism, plasma arginase activity was measured in patients and controls. Plasma arginase activity was significantly elevated in patients with sickle cell disease (n=140) compared to normal controls (n=45, $p<0.0001$; FIG. 1, Panel C), trended higher in patients with pulmonary hypertension (0.4±0.2 in normal controls; 1.9±1.7 vs. 2.7±2.5, sickle cell disease patients without pulmonary hypertension vs. sickle cell disease patients with pulmonary hypertension, $p=0.07$), and correlated to the arginine-to-ornithine ratio ($r=-0.33$, $p<0.001$, FIG. 1, Panel D). Arginase activity also significantly correlated to ADMA/arginine ($r=0.44$, $p<0.00001$), suggesting a link between arginase activity and increased methylated argninines. It is likely this link results from decreased arginine bioavailability for creatine synthesis due to high arginase activity, that leads to increased homocysteine levels as described in the background section, resulting in an elevation of ADMA. This cascade of events will decrease arginine bioavailability even further.

Arginase Activity and Associations with Clinical Markers. The relationship between arginase activity and clinical laboratory markers of disease severity was evaluated in order to identify mechanisms for increased enzymatic activity and associated effects on organ function (Table 8).

TABLE 8

Association with Arginase Activity as measured
by Spearman Rank Correlation Coefficient, r.*

| Category | Variable | R | N | p |
|---|---|---|---|---|
| Hemolysis | Cell-Free Hemoglobin | .55 | 136 | <0.001 |
|  | LDH | .35 | 121 | <0.001 |
|  | AST | .34 | 136 | <0..001 |
|  | Hematocrit | −.20 | 138 | 0.02 |
|  | Reticulocyte Count | .09 | 126 | 0.30 |
| Kidney | Creatinine | −.09 | 138 | 0.28 |
|  | Blood Urea Nitrogen | .08 | 138 | 0.33 |
| Liver | ALT | .19 | 138 | 0.03 |
|  | Alkaline Phosphatase | .07 | 137 | 0.40 |
|  | Albumin | .13 | 137 | 0.12 |
| Inflammation | WBC | .18 | 138 | 0.04 |
|  | Myeloperoxidase | .27 | 131 | 0.002 |
|  | Basophil Count | .15 | 138 | 0.08 |
|  | Monocyte Count | .03 | 138 | 0.71 |
|  | ESR | .04 | 100 | 0.72 |
|  | C-Reactive Protein | −.05 | 120 | 0.55 |
| Pulmonary | $O_2$ Sats | −.30 | 68 | 0.01 |
|  | TRV | .09 | 136 | 0.30 |
| Lipid | Triglycerides | .34 | 117 | <0.001 |
|  | Cholesterol | .19 | 122 | 0.03 |
| Adhesion | E-Selectin | .23 | 126 | 0.008 |
|  | P-Selectin | .33 | 135 | <0.001 |
|  | VCAM | .27 | 137 | 0.001 |
|  | ICAM | .17 | 132 | 0.05 |
| Hematologic | % HbF | −.02 | 139 | 0.80 |
|  | % HbA | −.13 | 139 | 0.12 |
|  | % HbS | .11 | 139 | 0.19 |
|  | Platelet Count | .10 | 136 | 0.26 |

Figure 2:
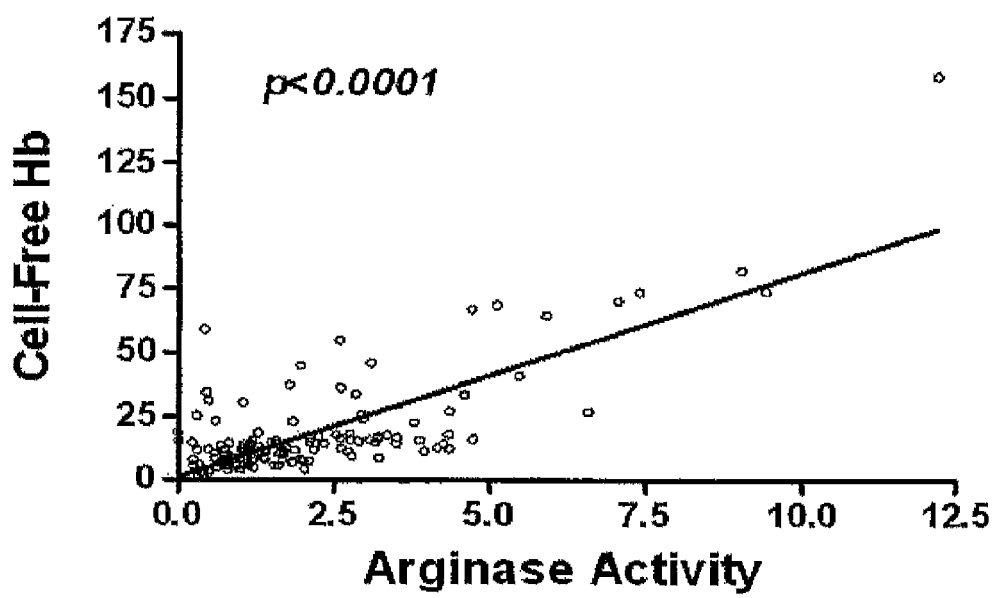
FIG. 2 is a set of graphs showing the association of arginase activity with hemolytic rate. Correlation of plasma arginase activity (μmol/ml/hr) to cell-free hemoglobin (*Cell-Free Hb*, $n=138$, $p<0.0001$; Panel A) and lactate dehydrogenase (LDH, n=121; $p<0.0001$; Panel B) in patients with sickle cell disease.
Figure 2:
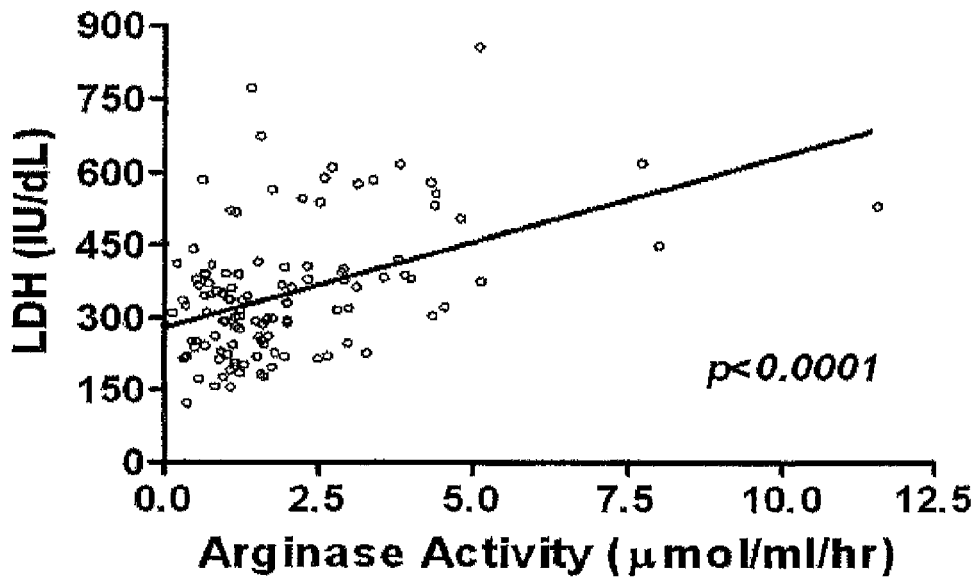

Plasma arginase activity was significantly associated with several markers of increased hemolytic rate (FIG. 2), including cell-free hemoglobin ($p<10^{-28}$, FIG. 2), lactate dehydrogenase (LDH, $p<0.001$), aspartate aminotransferase (AST, $p<0.001$), and hematocrit ($p=0.02$). Other significant associations included oxygen saturation, white blood cell count, myeloperoxidase, alanine aminotransferase (ALT), endothelial and platelet specific soluble adhesion molecules (sE-selectin, sP-selectin, sVCAM-1 and sICAM-1), triglycerides and cholesterol (Table 3A). No association of arginase activity with age ($r=-0.08$, $p=0.44$) or gender ($r=-0.07$, $p=0.44$) was identified. Elevated arginase activity did not correlate with markers of kidney function.

After bonferroni correction for multiple comparisons, cell-free hemoglobin, aspartate aminotransferase, triglycerides, P-selecting and soluble VCAM-1 remain significantly associated with elevated arginase activity in plasma. In multiple regression modeling, arginase activity was independently related to cell-free hemoglobin, sP-selectin and triglycerides (Table 9).

TABLE 9

Associations with $Log_{10}$ Arginase Activity in Multiple Regression Analysis.

| Category | Variable | r** | p** |
|---|---|---|---|
| Hemolysis | $Log_{10}$ LDH | 0.45 | <0.001 |
| Lipid | $Log_{10}$ Triglycerides | 0.32 | <0.001 |
| Adhesion | $Log_{10}$ P-selectin | 0.33 | <0.001 |

**Adjusted for the other independent variables in model; n = 101, $R^2$ = 0.40.

In these patients in steady state sickle cell disease, LDH levels more closely correlate with markers of intravascular hemolysis than liver dysfunction. LDH closely correlated with aspartate aminotransferase, which is released by both erythrocytes during hemolysis and hepatocytes, with an r value of 0.74 (p<0.0001) but less closely with alanine amino transferase (r=0.32; p<0.0001), which is specifically released by hepatocytes. LDH also correlated with all markers of high hemolytic rate, including high total and direct bilirubin levels (r=0.58; p<0.0001 and r=0.55; p<0.0001); low total hemoglobin and hematocrit levels (r=−0.55; p<0.0001 and r=−0.57; p<0.0001), and high absolute reticulocyte counts (r=0.42; p<0.0001). The lack of correlation between reticulocyte count and arginase in this cohort likely reflects the suppressive effects of transfusions, renal impairment and hydroxyurea therapy on reticulocytosis in the most severely affected patients. These data indicate that increased plasma arginase activity in sickle cell disease patients is associated with intravascular hemolysis, endothelial activation and inflammation.

Figure 3:
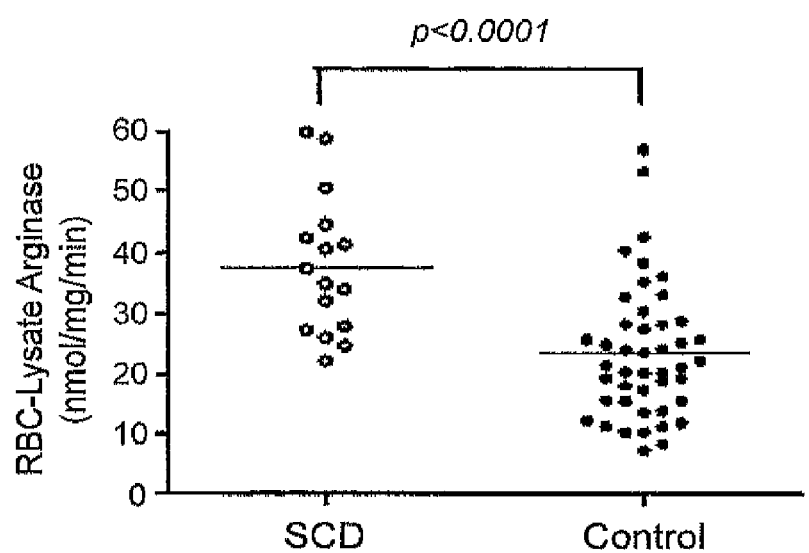
FIG. 3 is a set of graphs showing arginase activity in red blood cell lysate vs. plasma. Panel A. Red blood cell (RBC)-lysate arginase activity (nmol/mg/min) in normal controls (Control, n=45) compared to patients with sickle cell disease (SCD, n=16). Panel B. Correlation of plasma arginase to red blood cell-lysate arginase activity in both control patients (filled circles) and patients with sickle cell disease (open circles; r=0.43, p=0.0005). For purposes of comparison, horizontal and vertical dotted lines are set at approximately the $80^{th}$ percentile for arginase activities of RBC-lysates and plasma, respectively, for control patients.
Figure 3:
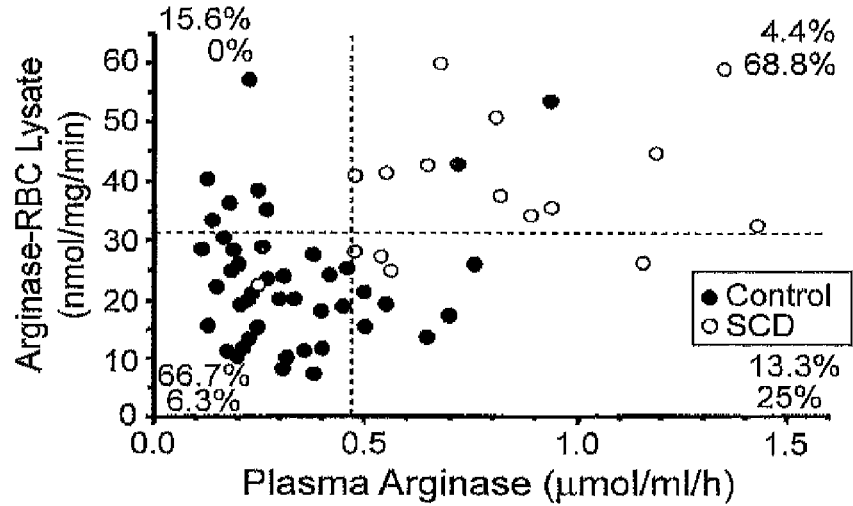

Arginase Activity in Red Blood Cells. In order to further identify the source of increased plasma arginase activity, arginase activities were determined also for red blood cell lysates of normal controls and a subset of patients with sickle cell disease (FIG. 3, Panel A). Arginase activity in red blood cell-lysate of patients with sickle cell disease was significantly higher than that of normal controls (p<0.0001) and correlated with arginase activity found in corresponding plasma (r=0.43, p=0.0005, FIG. 3, Panel B). For purposes of comparison, "normal range" boundaries were set arbitrarily at the 80th percentile for arginase activities of both red blood cell-lysates and plasma of control patients. Two-thirds of all control values fall within these boundaries, while in striking contrast, 94% of all values for plasma and erythrocyte arginase activities of sickle patients fall outside these boundaries (FIG. 3, Panel B).

Figure 4:
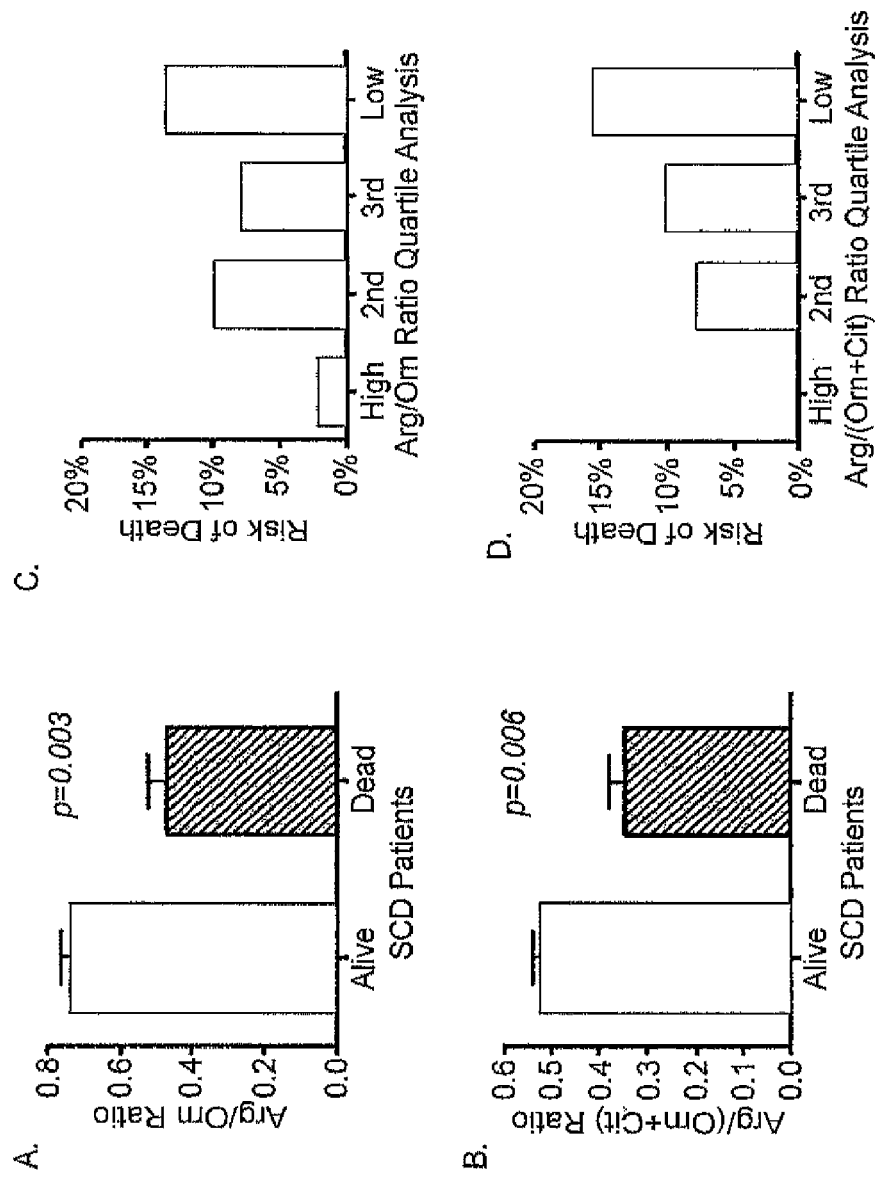
FIG. 4 is a set of graphs showing association of arginine bioavailability ratios with mortality in sickle cell disease. Panel A. Arginine-to-Ornithine (Arg/Orn) ratio and Panel B. Arginine/(Ornithine+Citrulline) ratio in surviving patients (Alive, n=192) with sickle cell disease (SCD) vs. patients who have died (Dead, n=17). Panel C. Arginine-to-Ornithine and Panel D. Arginine/(Ornithine+Citrulline) ratio quartile analysis of mortality risk (Risk of Death) over 44 months in patients with sickle cell disease.

Relationship of Dysregulated Arginine Metabolism to Mortality Rate. Since enrollment in the study, seventeen subjects have died as of October 2004, with median follow-up of 26 months for all subjects for whom follow-up information after the initial visit is available (n=194). Median survival time was 12 months for the 17 patients who died. Thirteen out of the 17 had an elevated tricuspid regurgitant jet velocity≧2.5 meters/second, and the presence of pulmonary hypertension by this definition was the most significant risk factor for death (risk ratio: 7.4; [2.4, 22.6], p<0.001). Plasma amino acid concentrations and plasma arginase activities are available for all 17 who died. Low ratios of plasma arginine-to-ornithine (p=0.03) and arginine-to-(ornithine+citrulline) (p=0.005), were associated with mortality in proportional hazards regression (Table 10). These ratios were an independent risk factor for death in this population, even after adjustment for tricuspid regurgitant jet velocity and renal insufficiency. In shifting L-arginine metabolism away from NO production and towards ornithine-dependent pathways, increased arginase activity contributes to events that put patients at risk for early death (FIG. 4).

TABLE 10

Proportional Hazards (Cox) Regression Analysis of Mortality

| Risk Factor | Total | Follow Up >0* | # of Deaths | p** | Risk Ratio (RR)** | 95% CI for RR |
|---|---|---|---|---|---|---|
| Low arginine/ornithine | 209 | 175 | 17 | .030 | 2.3 | (1.1, 4.9) |
| TR jet velocity ≧2.5 | 224 | 194 | 17 | <.001 | 7.4 | (2.4, 22.6) |
| Low arginine/ornithine, adjusted for TR jet velocity (<2.5 or ≧2.5) | 205 | 175 | 17 | .065 | 2.0 | (1.0, 4.1) |
| TR jet velocity ≧2.5, adjusted for arginine/ornithine | 205 | 175 | 17 | .001 | 6.3 | (2.0, 19.3) |
| Low arginine/ornithine, adjusted for TR jet velocity (<2.5 or ≧2.5) & $log_{10}$ creatinine | 203 | 174 | 17 | .054 | 2.2 | (1.0, 5.0) |
| Low arginine/(ornithine + citrulline) | 209 | 175 | 17 | .005 | 3.4 | (1.5, 7.7) |
| Low arginine/(ornithine + citrulline), adjusted for TR jet velocity (<2.5 or ≧2.5) | 205 | 175 | 17 | .011 | 2.9 | (1.3, 6.7) |
| TR jet velocity ≧2.5, adjusted for arginine/(ornithine + citrulline) | 205 | 175 | 17 | .002 | 6.0 | (2.0, 18.6) |
| Low arginine/(ornithine + citrulline), adjusted for TR jet velocity (<2.5 or ≧2.5) & $log_{10}$ creatinine | 203 | 174 | 17 | .026 | 2.6 | (1.1, 6.2) |

*First column shows total number of individuals for whom risk factor values are available, second shows number with follow-up time >0.
**Z-test on estimated coefficient divided by its standard error.
***For arginine/ornithine and arginine/(ornithine + citrulline), RR is given for $25^{th}$ relative to $75^{th}$ percentile (with all other independent variables held constant), calculated as $e^{coefficient \times (25th\ percentile\ -\ 75th\ percentile)}$. For TR jet velocity, RR is given for values ≧2.5 (coded 1) relative to values <2.5 (coded 0).
****Confidence interval.

These ratios were an independent risk factor for death in this population, even after adjustment for tricuspid regurgitant jet velocity and renal insufficiency. In shifting L-arginine metabolism away from NO production and towards ornithine-dependent pathways, increased arginase activity contributes to events that put patients at risk for early death (FIG. 4). The increased mortality risk ratio observed after citrulline was included in the Cox regression analysis probably reflects effects of renal dysfunction on arginine bioavailability. Indeed, citrulline levels trended higher in sickle cell disease patients with pulmonary hypertension and correlated with rising creatinine levels (r=0.54, p<0.001).

Citrulline is the endogenous precursor for de novo arginine synthesis, which occurs primarily within the kidney. The increased mortality risk ratio observed after citrulline was included in the Cox regression analysis probably reflects effects of renal dysfunction on arginine bioavailability. Indeed, citrulline levels trended higher in sickle cell disease patients with pulmonary hypertension and correlated with rising creatinine levels (r=0.54, p<0.001).

Example 5

Arginine/(Ornithine+Citrulline) Ratio and Cardiovascular Mortality Risk

Sequential subjects presenting to an emergency department with the complaint of chest pain were enrolled. Patients had baseline plasma levels of Arg, Ornithine and Citrulline, and the relationship with cardiovascular mortality risk was assessed at 1 year and 5 year outcomes.

The data presented in Table 11 show the differences in ratio of Arg/(ornithine+citrulline) vs mortality risks for the cohort. Note that a significantly lower ratio, indicative of a global arginine deficiency, is observed in subjects with increased cardiovascular mortality risk at both 1 year and 5 years.

TABLE 11

| | | Alive | Cardiovascular death | |
|---|---|---|---|---|
| Arg/(Ornithine + Citrulline) 1 year mortality data | N Mean S.D. Median Q1, Q3 (Min, Max) | 488 0.868 0.546 0.771 0.502, 1.1146 0.089, 6.010 | 48 0.588 0.339 0.525 0.374, 0.683 0.087, 1.583 | P < 0.001 (non-parametric) |
| Arg/(Ornithine + Citrulline) 5 year mortality data | N Mean S.D. Median Q1, Q3 (Min, Max) | 401 0.880 0.502 0.802 0.524, 1.127 0.095, 4.37 | 135 0.732 0.617 0.598 0.368, 0.830 0.087, 6.088 | P < 0.001 (non-parametric) |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for assessing efficacy of therapy of a human subject affected by a disease having elevated arginase activity, the method comprising:
   a) detecting a level of arginine and a level of a modulator of arginine bioavailability in a biological sample from the subject, wherein the biological sample is serum, plasma, blood, saliva, or urine;
   b) determining a ratio of the level of arginine to the level of the modulator of arginine bioavailability in a biological sample from the subject, wherein the modulator is one or more of ornithine, citrulline, symmetric dimethylarginine, asymmetric dimethylarginine, and $N^G$-monomethyl-L-arginine, wherein the biological sample is serum, plasma, blood, saliva, or urine,
   wherein the disease is asthma, sickle cell disease, pulmonary hypertension, or cardiovascular disease,
   wherein a ratio of the level of arginine to the level of the modulator of arginine bioavailability that is lower than a normal control ratio indicates elevated arginase activity, and
   c) assessing the efficacy of therapy be comparing the ratio before and after therapy, wherein an increase in the ratio compared to the ratio prior to the therapy, is indicative of efficacy of therapy in the subject.

2. The method of claim 1, wherein a ratio of the level of arginine to the level of the modulator of arginine bioavailability that is less than about 0.7 indicates the subject has low arginine bioavailability relative to a normal subject.

3. The method of claim 1, wherein a ratio of the level of arginine to the level of the modulator of arginine bioavailability that is equal to or greater than about 0.7 indicates normalization of arginine bioavailability in the subject.

4. The method of claim 1, wherein the pulmonary hypertension is primary pulmonary hypertension, secondary pulmonary hypertension, or persistent pulmonary hypertension of the newborn.

5. The method of claim 1, wherein the modulator includes ornithine.

6. The method of claim 5, wherein therapy is indicated as being efficacious when the therapy increases the arginine to ornithine ratio by at least 5%.

7. The method of claim 1, wherein the modulator includes asymmetric dimethylarginine.

8. The method of claim 1, wherein said determining comprises determining a ratio of the level of arginine to the level of at least two modulators of arginine bioavailability in the biological sample.

9. The method of claim 8, wherein the at least two modulators include ornithine and citrulline.

10. The method of claim 8, wherein the at least two modulators include ornithine and asymmetric dimethylarginine.

11. The method of claim 8, wherein the at least two modulators include asymmetric dimethylarginine and symmetric dimethylarginine.

12. The method of claim 1, comprising determining a ratio of the level of arginine to the level of at least three modulators of arginine bioavailability in the biological sample.

13. The method of claim 12, wherein the at least three modulators include ornithine, citrulline, and asymmetric dimethylarginine.

14. The method of claim 12, wherein the at least three modulators include ornithine, citrulline, and symmetric dimethylarginine.

15. The method of claim 12, wherein the at least three modulators include symmetric dimethylarginine, asymmetric dimethylarginine, and $N^G$-monomethyl-L-arginine.

16. The method of claim 1, further comprising determining a ratio of the sum of arginine plus creatine to the at least one modulator of arginine bioavailability in the biological sample.

17. The method of claim 1, wherein the cardiovascular disease is atherosclerosis, coronary artery disease, myocardial infarction, angina, stroke, or heart failure.

* * * * *